(12) United States Patent
Anderson et al.

(10) Patent No.: US 7,593,835 B2
(45) Date of Patent: Sep. 22, 2009

(54) REFORMULATED ATMOSPHERIC BAND MODEL METHOD FOR MODELING ATMOSPHERIC PROPAGATION AT ARBITRARILY FINE SPECTRAL RESOLUTION AND EXPANDED CAPABILITIES.

(75) Inventors: Gail P. Anderson, Boulder, CO (US); Alexander Berk, Canton, MA (US); Prabhat K. Acharya, Burlington, MA (US); Larry S. Bernstein, Lexington, MA (US); Steven M. Adler-Golden, Newtonville, MA (US); Jamine Lee, Burlington, MA (US); Leonid Muratov, Woburn, MA (US)

(73) Assignee: Spectral Sciences, Inc., Burlington, MA (US)

( * ) Notice: Subject to any disclaimer, the term of this patent is extended or adjusted under 35 U.S.C. 154(b) by 534 days.

(21) Appl. No.: 11/398,696

(22) Filed: Apr. 5, 2006

(65) Prior Publication Data
US 2007/0027664 A1    Feb. 1, 2007

Related U.S. Application Data

(63) Continuation-in-part of application No. 09/838,801, filed on Apr. 20, 2001, now Pat. No. 7,433,806.

(60) Provisional application No. 60/668,159, filed on Apr. 4, 2005.

(51) Int. Cl.
*G06F 17/10* (2006.01)
(52) U.S. Cl. .................... 703/2; 382/274; 73/23.37; 702/5
(58) Field of Classification Search ............. 703/2; 382/274; 73/23.37; 436/171, 181; 702/3, 702/5
See application file for complete search history.

(56) References Cited

U.S. PATENT DOCUMENTS

| | | | | |
|---|---|---|---|---|
| 5,315,513 A | * | 5/1994 | Abreu et al. | 702/3 |
| 5,884,226 A | * | 3/1999 | Anderson et al. | 702/3 |
| 6,584,405 B1 | * | 6/2003 | Moncet | 702/3 |
| 7,337,065 B2 | * | 2/2008 | Adler-Golden et al. | 702/3 |
| 7,433,806 B2 | * | 10/2008 | Berk et al. | 703/2 |

OTHER PUBLICATIONS

Amato et al., U. Fast Wavelet Radiative Transfer Model for Inversion of IASI Radiances, IEEE 2000 Int. Goescince and Remote Sensing Symposium, Jul. 2000, pp. 2797-2799.*
Thome et al., Atmospheric Correction of ASTER, IEEE Tranactions on Geoscience and Remote Sensing, vol. 36, No. 4, Jul. 1998, pp. 1199-1211.*
Zhengming et al., Effects of Temperature-Dependent Molecular Absorption Coefficients onn the Thermal Infrared Remote Sesning of the Earth Surface, IEEE Int. Geoscience and Remote Sensing Symposium, 1992, pp. 1242-1245.*

* cited by examiner

*Primary Examiner*—Russell Frejd
(74) *Attorney, Agent, or Firm*—Brian M. Dingman; Mirick, O'Connell, DeMallie & Lougee

(57) ABSTRACT

A radiative transport band model method for prediction and analysis of high spectral resolution radiometric measurements. Atomic and molecular line center absorption is determined from finite spectral bin equivalent widths. A mathematically exact expansion for finite bin equivalent widths provides high accuracy at any desired spectral resolution. The temperature and pressure dependent Voigt line tail spectral absorption contributing to each spectral bin is pre-computed and fit to Padé approximants for rapid and accurate accounting of neighboring-to-distant lines. A specific embodiment has been incorporated into the MODTRAN™ radiation transport model.

32 Claims, 8 Drawing Sheets

Spectral Absorbance (1 − Transmittance) for the Primary Sources of Atmospheric Extinction.

Figure 1. Spectral Absorbance (1 − Transmittance) for the Primary Sources of Atmospheric Extinction.

Figure 2. Illustration of LOS and Solar Illumination Paths.

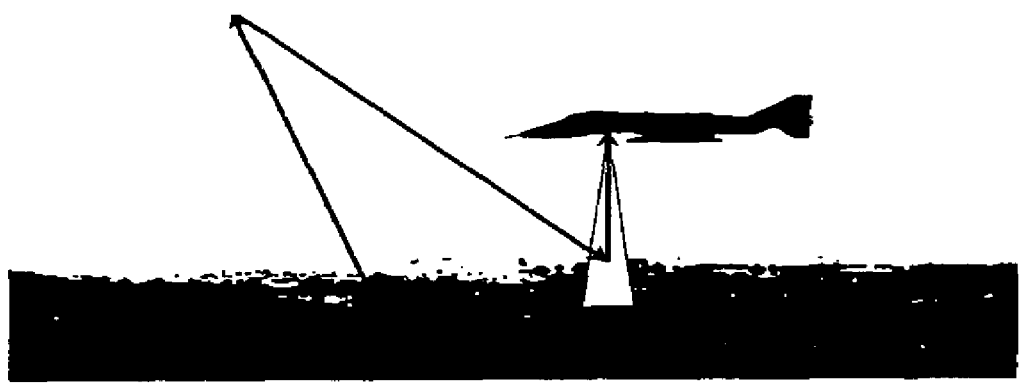
Figure 5. Illustration of missing photon trajectory if only diffuse transmittance is used in Eq. (68).

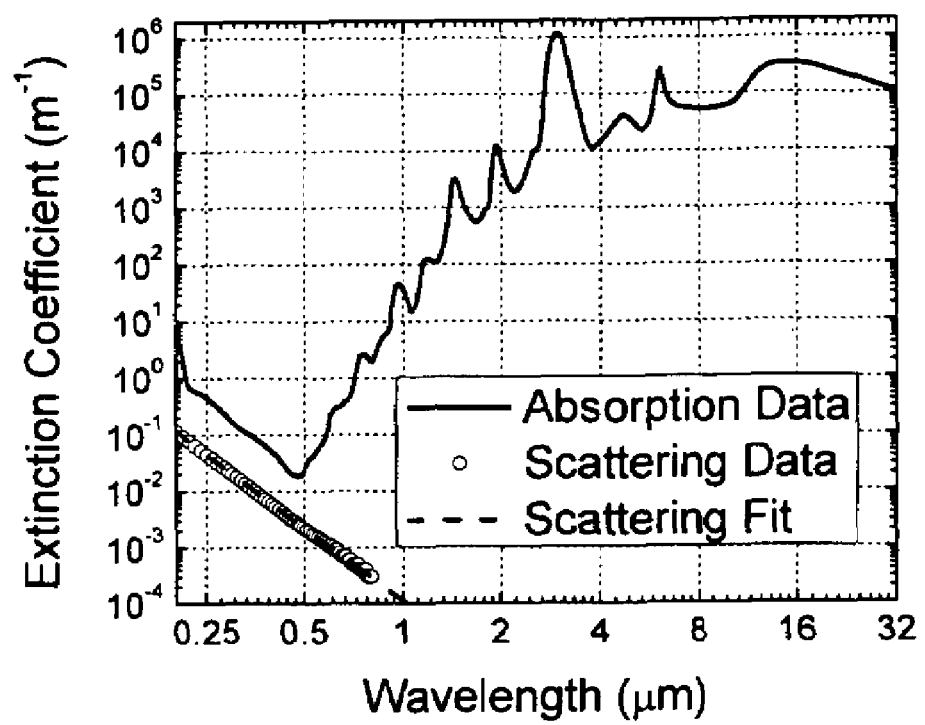
Figure 6. Spectral Absorption and Scattering Coefficients of Liquid Water.

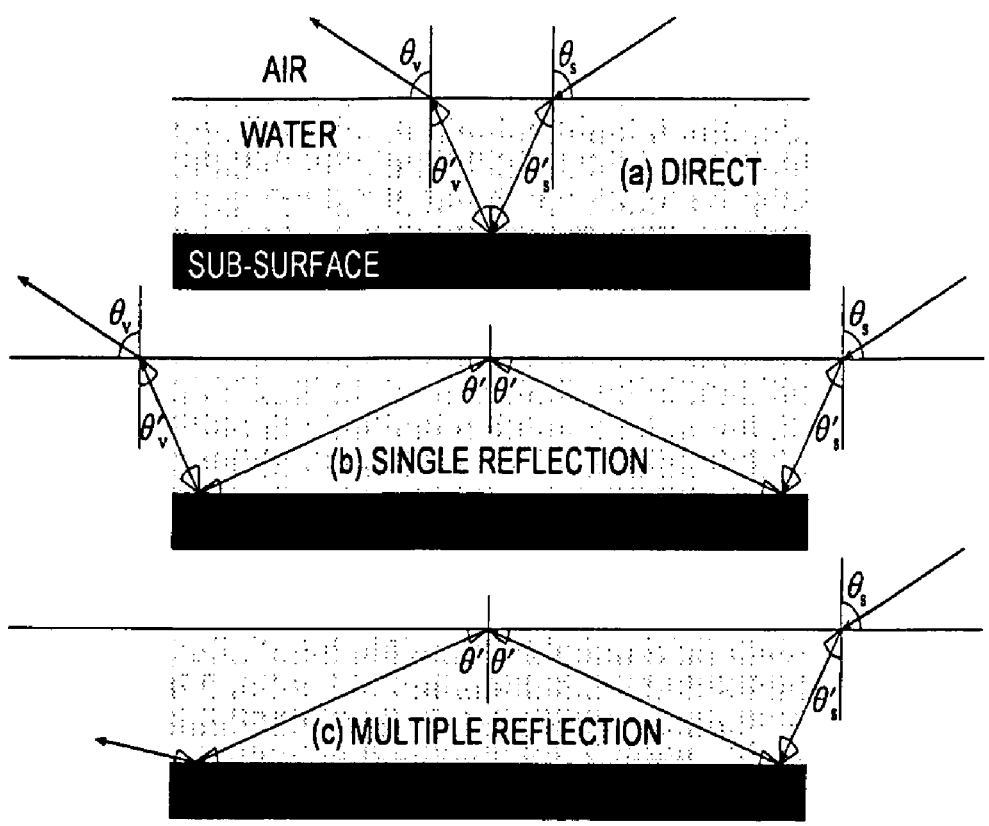
Figure 7. Illustration of direct and internal reflection paths without Rayleigh scattering by liquid water.

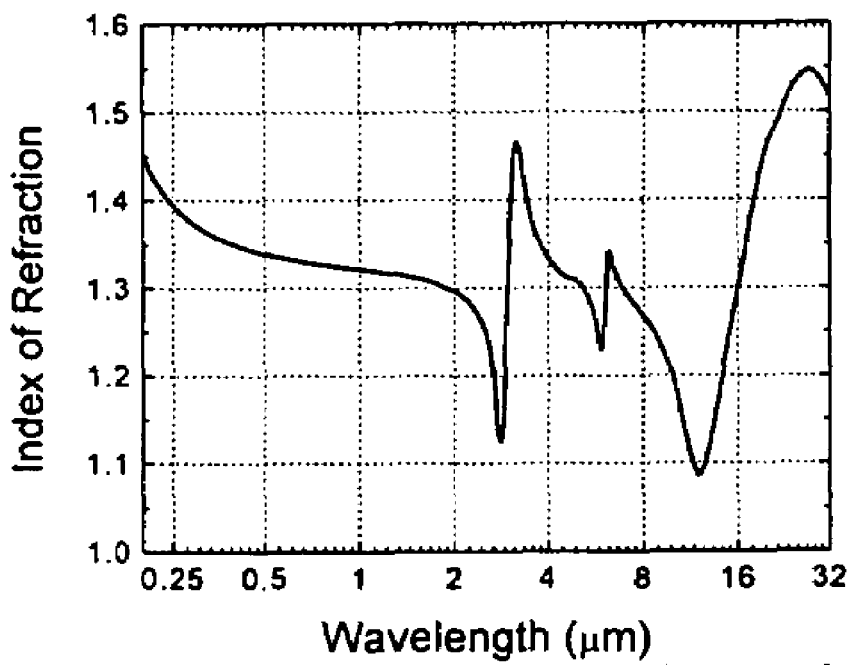
Figure 8. Liquid Water Spectral Index of Refraction.

REFORMULATED ATMOSPHERIC BAND MODEL METHOD FOR MODELING ATMOSPHERIC PROPAGATION AT ARBITRARILY FINE SPECTRAL RESOLUTION AND EXPANDED CAPABILITIES.

CROSS-REFERENCE TO RELATED APPLICATIONS

This application is a continuation in part of parent application Ser. No. 09/838,801 filed Apr. 20, 2001, now U.S. Pat. No. 7,433,806. Priority is claimed. The disclosure of the parent application is incorporated by reference herein. This application also claims priority of Provisional application Ser. No. 60/668,159 filed on Apr. 4, 2005

STATEMENT REGARDING FEDERALLY SPONSORED RESEARCH

This invention was made with government support under contracts F19628-02-C-0078 and FA8718-04-C-0073 awarded by the Department of the Air Force. The government has certain rights in this invention.

FIELD OF THE INVENTION

This invention relates to a radiative transport band model for application to high spectral resolution simulations.

BACKGROUND OF THE INVENTION

Calculation of in-band radiances via the line-by-line (LBL) approach is computationally intensive. Not only does it require the calculation of spectral molecular absorption coefficients for the series of pressure and temperature pairs encountered in the specified atmosphere, but it also requires the radiation transport equation (RTE) be solved for each spectral point. Because of the fine structure of molecular absorption, especially at higher altitudes (lower pressures), a very finely spaced spectral grid is required. Spectral step size depends upon scenario and accuracy requirements, but values of between 0.01 and 0.00001 $cm^{-1}$ is common.

The MODTRAN™ solution to this problem is to use a narrow statistical band model. In this approach, the RTE is solved for a relatively narrow spectral band all at once. A number of physical and statistical approximations are made. The quality of the MODTRAN™ results depend largely upon the validity of these approximations for any specific scenario. Over the past 30 years of MODTRAN™ development, much effort has been focused on fine tuning the model to improve accuracy for the terrestrial atmosphere. An earlier version of MODTRAN is described in U.S. Pat. No. 5,884,226.

The integral RTE defines the line-of-sight (LOS) monochromatic diffuse radiant intensity $I_\nu(\Omega_0;0)$ at spectral frequency $\nu$ along a refracted path in the direction specified by solid angle $\Omega_0$:

$$I_\nu(\Omega_0; 0) = e^{-\tau_\nu(s)} I_\nu(\Omega_s; s) + \int_0^{\tau_\nu(s)} e^{-\tau_\nu(s')} J_\nu(\Omega_{s'}; s') d\tau_\nu(s'). \quad (1)$$

This equation states that the observed spectral radiant intensity at the sensor (s=0) equals the spectral radiant intensity directed towards the sensor a distance s away along the refracted path attenuated by the foreground path transmittance $e^{-\tau_\nu(s)}$ plus the integral of intervening source radiation $J_\nu(\Omega_{s'};s')$ attenuated by its foreground transmittance $e^{-\tau_\nu(s')}$. The path spectral transmittances in Eq. (1) are defined in terms of dimensionless optical depths, $\tau_\nu(s)$. The optical depth terms themselves are path integrals over extinction coefficients, $b_\nu(s')$ [units of reciprocal length].

$$\tau_\nu(s) \equiv \int_0^s b_\nu(s') ds' \quad (2)$$

The extinction coefficients consists of absorption $b_\nu^{abs}(s)$ and scattering $b_\nu^{sct}(s)$ components, which are computed as sums over atmospheric molecular and particulate species contributions $b_{\nu,i}(s)$.

$$b_\nu(s) \equiv b_\nu^{abs}(s) + b_\nu^{sct}(s) \quad (3)$$
$$\equiv \sum_{i\, species} [b_{\nu,i}^{abs}(s) + b_{\nu,i}^{sct}(s)]$$
$$\equiv \sum_{i\, species} [\kappa_{\nu,i}^{abs}(s) + \kappa_{\nu,i}^{sct}(s)] \rho_i(s)$$

The individual species absorption and scattering coefficients are themselves the product of a cross-section $\kappa_{\nu,i}(s)$ [units of area] and a density $\rho_i(s)$ [number per unit volume].

The atmospheric source term $J_\nu(\Omega_s;s)$ consists of three distinct components: local thermal emission, single scattered directly transmitted solar (and/or lunar) irradiance and diffuse radiation scattered into the LOS $$J_\nu(\Omega_s; s) = \frac{b_\nu^{abs}}{b_\nu(s)} B_\nu(T_s) + \quad \text{local thermal emission} \quad (4)$$
$$\frac{b_\nu^{sct}}{b_\nu(s)} p_\nu(\Omega_s, \Omega_s^{sun}; s) e^{-\tau_\nu^{sun}(s)} F_\nu^{sun} + \quad \text{single scatter solar}$$
$$\frac{b_\nu^{sct}(s)}{b_\nu(s)} \int_{4\pi} p_\nu(\Omega_s, \Omega'; s) I_\nu(\Omega'; s) d\Omega' \quad \text{multiple scatter.}$$

The first term, the thermal emission, is the product of the Planck blackbody function $B_\nu(T_s)$ at local temperature $T_s$ and the local emissivity, which is represented as a ratio of absorption to extinction coefficients. This expression for thermal emission assumes local thermodynamic equilibrium (LTE) conditions—an assumption, valid in the lower terrestrial atmosphere, that molecular collisions occur in sufficient frequency to control upper state population densities.

The latter two terms in Eq. (4) are the path scattered radiance. The single scatter solar radiation is the product of the top-of-atmosphere (TOA) solar irradiance $F_\nu^{sun}$, the scattering point to sun transmittance $e^{-\tau_\nu^{sun}(s)}$, the effective scattering phase function $p_\nu(\Omega_s,\Omega_s^{sun};s)$, and the single scattering albedo, equal to the ratio of scattering to extinction coefficients. The multiply scattered radiation is the integral over all directions ($4\pi$ steradians) of the incoming diffuse radiation scattered into the LOS. The dependence of the multiple scattering on path radiance itself significantly complicates the radiation transport equation, transforming it into a fully coupled problem. MODTRAN™ uses the DISORT model (below), a discrete ordinate algorithm, to solve the coupled equations. The effective phase function that appears in both scattered radiance source terms is a scattering coefficient weighted average of individual species i scattering phase functions $p_{v,i}(\Omega_s, \Omega_s'; s)$:

$$p_v(\Omega_s, \Omega_s'; s) \equiv \frac{\sum_{i \, species} b_{v,i}^{sct}(s) p_{v,i}(\Omega_s, \Omega_s'; s)}{b_v^{sct}(s)} \quad (5)$$

The phase functions of Eq. (4) are all unit normalized, with dimensions of reciprocal steradians (1/sr). It is somewhat more common to define phase functions as dimensionless with a $4\pi$ sr normalization, but MODTRAN™ uses the unit normalization to eliminate all constant factors from the source function equation.

Substituting the source term of Eq. (4) into the integral RTE, the spectral radiant intensity of Eq. (1) can be rewritten as absorption optical depth $\tau_v^{abs}(s)$ and scattering optical depth $\tau_v^{sct}(s)$ integrals:

$$I_v(\Omega_0; 0) = e^{-\tau_v(s)} I_v(\Omega_s; s) + \int_0^{\tau_v^{abs}(s)} e^{-\tau_v(s')} B_v(T_{s'}) d\tau_v^{abs}(s') + \int_0^{\tau_v^{sct}(s)} e^{-\tau_v(s')} \left[ \begin{array}{c} p_v(\Omega_{s'}, \Omega_{s'}^{sun}; s') e^{-\tau_v^{sun}(s')} F_v^{sun} + \\ \int_{4\pi} I_v(\Omega'; s') p_v(\Omega_{s'}, \Omega'; s') d\Omega' \end{array} \right] d\tau_v^{sct}(s'); \quad (6)$$

$$\tau_v^{abs}(s) \equiv \int_0^s b_v^{abs}(s') ds' \text{ and } \tau_v^{sct}(s) \equiv \int_0^s b_v^{sct}(s') ds'.$$

For band model theory, the key atmospheric attenuation parameter is the transmittance itself, not the optical depth. For that reason, it is convenient to again rewrite the RTE in terms of transmittance, $t_v(s) = \exp[-\tau_v(s)]$, integrals:

$$I_v(\Omega_0; 0) = t_v(s) I_v(\Omega_s; s) + \int_{t_v^{abs}(s)}^1 t_v^{sct}(s') B_v(T_{s'}) dt_v^{abs}(s') + \int_{t_v^{sct}(s)}^1 t_v^{abs}(s') \left[ \begin{array}{c} p_v(\Omega_{s'}, \Omega_{s'}^{sun}; s') t_v^{sun}(s') F_v^{sun} + \\ \int_{4\pi} I_v(\Omega'; s') p_v(\Omega_{s'}, \Omega'; s') d\Omega' \end{array} \right] dt_v^{sct}(s'). \quad (7)$$

Within MODTRAN™, the boundary radiant intensity term $I_v(\Omega_s; s)$ for the full LOS path is typically zero unless the path terminates at the spherical Earth surface. There is an option to include grey body emission with no reflected source at the path final altitude. For a down-looking sensor whose LOS intersects the ground, the surface radiance includes both emissive and reflective components:

$$I_v(\Omega_s; s) = \varepsilon_v(\Omega_s; s) B_v(T_g) + \quad \text{Surface emission} \quad (8)$$
$$\mu_s^{sun} f_v(\Omega_s, \Omega_s^{sun}; s) t_v^{sun}(s) F_v^{sun} + \quad \text{Reflected directly transmitted solar irradiance}$$
$$\int_{2\pi} I_v(\Omega'; s) f_v(\Omega_s, \Omega'; s) \mu' d\Omega' \quad \text{Reflected downward flux}$$

In this equation, $\mu'$ is the cosine of the zenith angle of incoming radiation measured from the ground, $f_v(\Omega_s, \Omega'; s)$ is the surface bi-direction reflectance distribution function (BRDF) in units of reciprocal steradians at ground location s, $\varepsilon_v(\Omega_s; s)$ is the dimensionless directional emissivity in the LOS path direction at s, and the surface reflected downward flux is computed as the upper hemisphere integral ($2\pi$ sr) over incoming diffuse radiation. The BRDF defines the reflected radiance resulting from surface illumination as a function of both incoming and outgoing angles, and it is normalized to the surface albedo $\alpha_v(s)$:

$$\alpha_v(s) = \frac{1}{\pi} \int_{2\pi} \int_{2\pi} f_v(\Omega, \Omega'; s) \mu' d\Omega' \mu d\Omega \quad (9)$$

The directional emissivity, the complement of the directional reflectivity $\rho_v(\Omega_s)$, dictates the angular distribution of the surface thermal emission, and is computed directly from the BRDF by the following relationship:

$$\varepsilon_v(\Omega_s; s) \equiv 1 - \rho_v(\Omega_s; s) = 1 - \int_{2\pi} f_v(\Omega_s, \Omega'; s) \mu' d\Omega' \quad (10)$$

Finally, the Earth viewing radiance is obtained by substituting the surface radiance term, Eq. (8), into the RTE, Eq. (7):

$$I_v(\Omega; 0) = t_v(s) I_v(\Omega; s) + \int_{t_v^{abs}(s)}^1 t_v^{sct}(s') B_v(T_{s'}) dt_v^{abs}(s') + \int_{t_v^{sct}(s)}^1 t_v^{abs}(s') \left\{ \begin{array}{c} t_v^{sun}(s') F_v^{sun} p_v(\Omega, \Omega^{sun}; s') + \\ \int_{4\pi} I_v(\Omega'; s) p_v(\Omega, \Omega'; s') d\Omega' \end{array} \right\} dt_v^{sct}(s'); \quad (11)$$

$$I_v(\Omega; s) = \varepsilon_v(\Omega; s) B_v(T_g) + \int_{2\pi} [t_v^{sun}(s) F_v^{sun} \delta(\Omega - \Omega^{sun}) + I_v(\Omega'; s)]$$
$$f_v(\Omega, \Omega'; s) \mu' d\Omega' \text{ if } s = s_g.$$

In writing this final set of equations, the explicit dependence of the solid angle $\Omega$ on position s has been dropped for notational simplicity and the Dirac delta function $\delta(\Omega - \Omega^{sun})$ has been introduced to move the surface direct solar illumination term inside the angular integration. There is also an implicit understanding that the boundary term $I_v(\Omega; s)$ is zero unless the path actually terminates at the ground, $s = s_g$. Eq. (11) serves as the starting point for the derivation of the MODTRAN™ band model.

The MODTRAN™ Band Model

The MODTRAN™ band model approach is concerned with calculation of narrow spectral bin radiant intensities $<I_0(\Omega)>$:

$$\langle I_0(\Omega) \rangle \equiv \frac{1}{\Delta v} \int_{\Delta v} I_v(\Omega; 0) dv \quad (12)$$

The width $\Delta v$ of the band model spectral bin should be selected sufficiently narrow to insure no more than a modest variation in all spectral data other than molecular absorption. This definition enables all the spectrally smoothly varying properties to be modeled with an effective band value, computed either as an interval average or central value. A smaller band width typically produces finer accuracy. The reformulated band model incorporated into MODTRAN™, described in the parent application which is incorporated herein by reference, provides 4 band model resolution options, 0.1, 1.0, 5.0 and 15.0 cm$^{-1}$. With an over-line used to represent an effective band value, the band model complement to the LBL LOS radiance expression, Eq. (11), has the following form:

$$\langle I_0(\Omega) \rangle = \langle t_{0\to s} I_s(\Omega) \rangle - \int_0^s \overline{t_{0\to s'}^{sct}} \overline{B(T_{s'})} \frac{d\left[\overline{t_{0\to s'}^{part\_abs}} \langle \overline{t_{0\to s'}^{mol\_abs}} \rangle \right]}{ds'} ds' -$$

$$\int_0^s \overline{t_{0\to s'\to sun}^{part\_abs}} \langle \overline{t_{0\to s'\to sun}^{mol\_abs}} \rangle \overline{t_{s'\to sun}^{sct}} \overline{F^{sun}} \overline{p_{s'}}(\Omega, \Omega^{sun}) \left( \frac{d\overline{t_{0\to s'}^{sct}}}{ds'} \right) ds' -$$

$$\int_0^s \overline{t_{0\to s'}^{part\_abs}} \left\langle \overline{t_{0\to s'}^{mol\_abs}} \int_{4\pi} I_{s'}(\Omega') \overline{p_{s'}}(\Omega, \Omega') d\Omega' \right\rangle \left( \frac{d\overline{t_{0\to s'}^{sct}}}{ds'} \right) ds' \quad (13)$$

*BoundaryCondition*

$$\langle t_{0\to s} I_s(\Omega) \rangle = \overline{\varepsilon_s}(\Omega) \overline{t_{0\to s}^{sct}} \overline{B(T_g)} \overline{t_{0\to s'}^{part\_abs}} \langle \overline{t_{0\to s}^{mol\_abs}} \rangle +$$

$$\overline{t_{0\to s\to sun}^{sct}} \overline{t_{0\to s\to sun}^{part\_abs}} \langle \overline{t_{0\to s\to sun}^{mol\_abs}} \rangle \overline{F^{sun}} \overline{f_s}(\Omega, \Omega^{sun}) \mu^{sun} +$$

$$\overline{t_{0\to s}^{sct}} \overline{t_{0\to s}^{part\_abs}} \left\langle \overline{t_{0\to s}^{mol\_abs}} \int_{2\pi} I_s(\Omega') \overline{f_s}(\Omega, \Omega') \mu' d\Omega' \right\rangle.$$

In these equations, the LOS integrands are expressed as functions of the refractive path length s'. Furthermore, the attenuation resulting from absorption is partitioned into its molecular and particulate contributions. The labeling of the band-averaged absorption as arising solely from particulate sources is somewhat misleading. Detailed line compilation data is unavailable for some molecular species, especially large molecules such as the chlorofluorocarbons (CFC's). For these species, absorption is modeled via relatively coarse spectral resolution cross-section data. The resulting transmittances are band averaged values and included in the $\overline{t^{part\_abs}}$ terms.

Eq. (13) is the fundamental narrow band model radiance equation. It explicitly partitions the spectral data for which effective band values are used from the highly spectrally varying molecular absorption contributions. The effective coarse spectral resolution band data falls into three categories.

1. Ground properties: The surface emissivity $\overline{\varepsilon_s}$ and the surface BRDF $\overline{f_s}$;
2. Particulate, Molecular Cross-Section & Rayleigh data: The scattering phase function $\overline{p_{s'}}$ and the atmospheric attenuation resulting from scattering $\overline{t^{sct}}$ and particulate (and molecular cross-section) absorption $\overline{t^{part\_abs}}$; and
3. Source functions: The Planck blackbody function $\overline{B}$ and the TOA solar irradiance $\overline{F^{sun}}$.

The ground is comprised of solids and liquids. Employing lower spectral resolution surface data is justified because condensed matter does not exhibit the fine spectral structure of molecular gas absorption. Similarly, even though scattering data can be highly structured for a collection of particles of a specific size and shape; terrestrial aerosols and clouds consist of particulates of various size, shape and orientation. These distributions smooth out the fine spectral structure. Rayleigh scattering optical properties are also spectrally smoothly varying, and the molecular cross-section data is modeled as spectrally smoothly varying in the absence of accurate fine spectral resolution information. The variation of the Planck blackbody function at atmospheric temperatures (~180 to 305K) for the MODTRAN™ band model widths is modest for the spectral range over which thermal emission is significant.

The one term for which spectral averaging is somewhat suspect is the TOA solar irradiance. The sun is essentially a ~6000K blackbody; however, molecular absorption within the solar atmosphere generates Fraunhofer structure. Two facts help support the spectral averaging of the solar data approximation: (1) The spectral correlation between the solar spectrum and the Earth atmospheric absorption is well represented as randomly correlated for most spectral bins; and (2) The current state-of-the-art in measurement and calculation of TOA solar irradiances suggests that spectral structure assignments finer than ~1 cm$^{-1}$ are unreliable.

Currently, the multiple scattering (MS) algorithms within MODTRAN™ only support specification of surface reflectance via an angularly independent spectral albedo, $f_v(\Omega,\Omega'; s)=\alpha_v(s)/\pi$. Given this limitation, the surface reflected downward flux is approximated as a product of the directional reflectivity and the hemisphere integrated downward flux, $F_v^\downarrow(s)$:

$$\int_{2\pi} I_v(\Omega'; s) f_v(\Omega, \Omega'; s) \mu' d\Omega' \cong \quad (14)$$

$$\rho_v(\Omega; s) F_v^\downarrow(s) \equiv \rho_v(\Omega; s) \int_{2\pi} I_v(\Omega'; s) \mu' d\Omega'.$$

This expression for the reflected downward flux is quite reasonable if the distribution of downward diffuse radiance is nearly homogeneous or the surface reflectance nearly Lambertian. On the other hand, for clear sky solar illumination of a specular surface such as still water, Eq. (14) is a poor approximation; however, in this case, the observed radiance will be dominated by the direct solar illumination and the error in total observed radiance may still be small. Merging the flux approximation into the narrow band model radiance expression, Eq. (13), the surface reflected diffuse radiance term factors as follows:

$$\left\langle \overline{t_{0\to s}^{mol\_abs}} \int_{2\pi} I_s(\Omega') \overline{f_s}(\Omega, \Omega') \mu' d\Omega' \right\rangle \cong \overline{\rho_s}(\Omega) \langle \overline{t_{0\to s}^{mol\_abs}} F_v^\downarrow(s) \rangle. \quad (15)$$

When MODTRAN™ utilizes its correlated-k (CK) option, an algorithm that recasts the molecular band model into weighted sum of monochromatic calculations, the path radiant intensity computation follows the prescription of Eq. (13) with the caveat of Eq. (15). However, further approximations are necessary if the band model algorithm is used without CK. The issue here is that the MODTRAN™ atmospherically scattered diffuse radiance and the downward surface flux terms are computed from the MS algorithms within MODTRAN™. These MS algorithms were developed to solve the coupled monochromatic radiation transport problem, and they rely heavily upon Beer's Law. Beer's Law states that the spectral transmittance of a multi-segmented path equals the product of the individual segment transmittances:

$$t_\nu(0 \to s' \to s) = t_\nu(0 \to s') \, t_\nu(s' \to s). \quad (16)$$

Alternatively stated, segment extinction optical depths are additive. This relationship does hold for CK transmittances but not for band model in-band transmittances:

$$\langle t_{0 \to s' \to s} \rangle \neq \langle t_{0 \to s} \rangle \langle t_{s' \to s} \rangle. \quad (17)$$

When the CK option is not invoked, MODTRAN™ proceeds with multiple scatter source term and level flux calculations computed from a Beer's Law model even though the layer optical depths are poorly defined. The inaccuracy of this approach is limited somewhat by combining the MS source terms with foreground transmittances computed for the inhomogeneous path. Thus, the LOS radiance terms containing diffuse radiation are calculated as follows:

$$\begin{aligned} \langle t_{0 \to s}^{\text{mol\_abs}} F_s^\downarrow \rangle &\cong \langle t_{0 \to s}^{\text{mol\_abs}} \rangle \langle F_s^\downarrow \rangle & \text{band model} \\ \langle t_{0 \to s'}^{\text{mol\_abs}} \int_{4\pi} I_{s'}(\Omega') \overline{p_{s'}}(\Omega, \Omega') d\Omega' \rangle &\cong \langle t_{0 \to s}^{\text{mol\_abs}} \rangle \int_{4\pi} \langle I_{s'}(\Omega') \rangle \overline{p_{s'}}(\Omega, \Omega') d\Omega' & \text{with no } CK \end{aligned} \quad (18)$$

Together, Eqs. (13), (15) and (18) define the MODTRAN™ path radiance formulation. However, implementation of the approach still requires a description of three key model components: the MODTRAN™ statistical band model molecular transmittance calculation, the multiple scattering algorithms, and the surface water model. Descriptions of these components follow.

SUMMARY OF THE INVENTION

This invention comprises an improved band model method for modeling atmospheric propagation at arbitrarily fine spectral resolution, sometimes termed herein as "Improvements to MODTRAN4™". Featured in the invention is a method for predicting atmospheric radiation transport parameters including transmittance and radiance, comprising defining one or more conditions under which the atmospheric transmittance and radiance will be predicted, providing atomic and molecular transition data for a given spectral range and atmospheric conditions, dividing the spectral region into a number of spectral bins that determine the spectral resolution, each bin having a width of less than $1.0 \text{ cm}^{-1}$, calculating atomic and molecular species line center absorption from at least the equivalent width of the atomic and molecular transitions centered within each spectral bin, calculating line tail absorption within each spectral bin from atomic and molecular transitions not centered within the bin, and determining atomic and molecular species spectral transmittances for each spectral bin, the spectral transmittance having a value which is a function of at least the calculated line center absorptions and the calculated line tail absorptions.

The spectral bins may have a width of about $0.1 \text{ cm}^{-1}$. The step of calculating line center absorption may include calculating, from an exact expansion, the bin Voigt equivalent width of atomic and molecular transitions whose centers lie within each spectral bin. The exact expansion may be an exact modified Bessel functions expansion. The calculating line tail absorption step may include subtracting line-tail absorption as calculated from the column strength, the Lorentz half-width, the Doppler half-width, and the line tail spectral displacement. The calculating line center absorption step may include determining the Voigt line-shape function computed at specific frequencies.

The line tail calculation step may include calculating line tail absorption within each bin from atomic and molecular transitions centered outside of the bin using Padé approximant spectral fits to Voigt absorption coefficient curves. The line tail absorption calculation step may include determining a database of temperature and pressure dependent Padé approximant spectral fits to Voigt absorption coefficient curves. There may be five Padé parameters. The Padé parameters may be determined from summed line tail spectral absorption coefficients. One Padé parameter may be determined at the center of the bin, and one at each edge of the bin. One Padé parameter may be the derivative of the absorption coefficient with respect to the normalized spectral variable at the line center. One Padé parameter may be the integral of the spectral absorption coefficient over the spectral band. The Padé parameters database may be generated for a plurality of temperatures. The Padé parameters database may be determined for a plurality of pressures. The line center absorptions may be calculated from atomic and molecular transitions centered no more than half a spectral bin width from the bin, and the line tail absorptions are calculated from atomic and molecular transitions not centered within a half spectral bin from the bin.

The conditions may comprise atmospheric species for which transition data is provided. Band model data may be provided for at least some of the species. Absorption cross section data may be provided for at least some of the species. The conditions may comprise an arbitrary quantity of species for which transition data is provided. The conditions may comprise a surface water model. The surface water model may introduce a spectral attenuation layer. The surface water model may predict surface leaving radiances due to surface water.

The defining step may comprise allowing the user to define the radiation refractive path through the atmosphere. The refractive path may comprise a circular arc. The conditions may comprise the aerosol spectral optical properties. The properties can preferably be varied as a function of altitude. The properties may comprise spectral extinction, spectral scattering and spectral phase function. The method may further comprise determining the medium embedded diffuse transmittance.

Featured in another embodiment of the invention is a method for predicting atmospheric radiation transport parameters including transmittance and radiance, comprising defining one or more conditions under which the atmospheric transmittance and radiance will be predicted, wherein the conditions comprise an arbitrary number of atmospheric species for which transition data is provided, a surface water model, a user-defined radiation refractive path through the atmosphere, and the aerosol spectral optical properties, providing atomic and molecular transition data for a given spectral range and atmospheric conditions, dividing the spectral region into a number of spectral bins that determine the spectral resolution, each bin having a width of less than $1.0$ cm$^{-1}$, calculating atomic and molecular species line center absorption from at least the equivalent width of the atomic and molecular transitions centered within each spectral bin, calculating line tail absorption within each spectral bin from atomic and molecular transitions not centered within the bin, determining atomic and molecular species spectral transmittances for each spectral bin, the spectral transmittance having a value which is a function of at least the calculated line center absorptions and the calculated line tail absorptions, and determining the medium embedded diffuse transmittance.

A primary use of the invention is spectral exploitation. More specifically, this invention greatly enhances the ability to perform the radiation transport necessary to accurately atmospherically correct airborne and satellite imagery of the Earth. Thus, a user can accurately translate the at-sensor observed radiances (i.e. an image captured by an airborne or space-based image sensor) into at-ground spectral reflectances and emissivities. When accurately determined, the spectral exploitation scientists can use the retrieved surface reflectances to classify and identify materials on the Earth. Applications are many including tracking of crop health, monitoring of the littoral zone, mapping of mineral fields, and detecting military targets.

BRIEF DESCRIPTION OF THE DRAWINGS

Other objects, features and advantages will occur to those skilled in the art from the following description of the preferred embodiments and the accompanying drawings in which:

FIG. 5 is an illustration of missing photon trajectory, useful in understanding an aspect of the invention.

FIG. 6 is a plot of spectral absorption and scattering coefficients of liquid water, useful in understanding aspects of the invention.

FIG. 7 is three illustrations of reflections by liquid water, useful in understanding aspects of the invention.

FIG. 8 is a plot of liquid water spectral index of refraction, useful in understanding aspects of the invention.

DETAILED DESCRIPTION OF THE PREFERRED EMBODIMENTS OF THE INVENTION

IMPROVEMENTS TO MODTRAN4™ Molecular Transmittance

SERTRAN, the Spectral Enhanced Resolution band model IMPROVEMENT TO MODTRAN4™, is statistical. SERTRAN is described in detail in the parent patent application incorporated herein by reference. MODTRAN™ does not account for the exact location of molecular transitions and the distribution of their line strengths within each spectral bin. Instead, these distributions are modeled statistically. In this spirit, the formulation of the molecular transmittance calculation begins with the stipulation that the spectral bin molecular absorption from distinct species is randomly correlated, so that the combined species molecular transmittance $\langle t^{mol\_abs} \rangle$ for a band model spectral bin can be computed as a product of individual band model species transmittances $\langle t^{k\_abs} \rangle$:

$$\langle t^{mol\_abs} \rangle = \prod_{k\,mol} \langle t^{k\_abs} \rangle. \tag{19}$$

Figure 1:
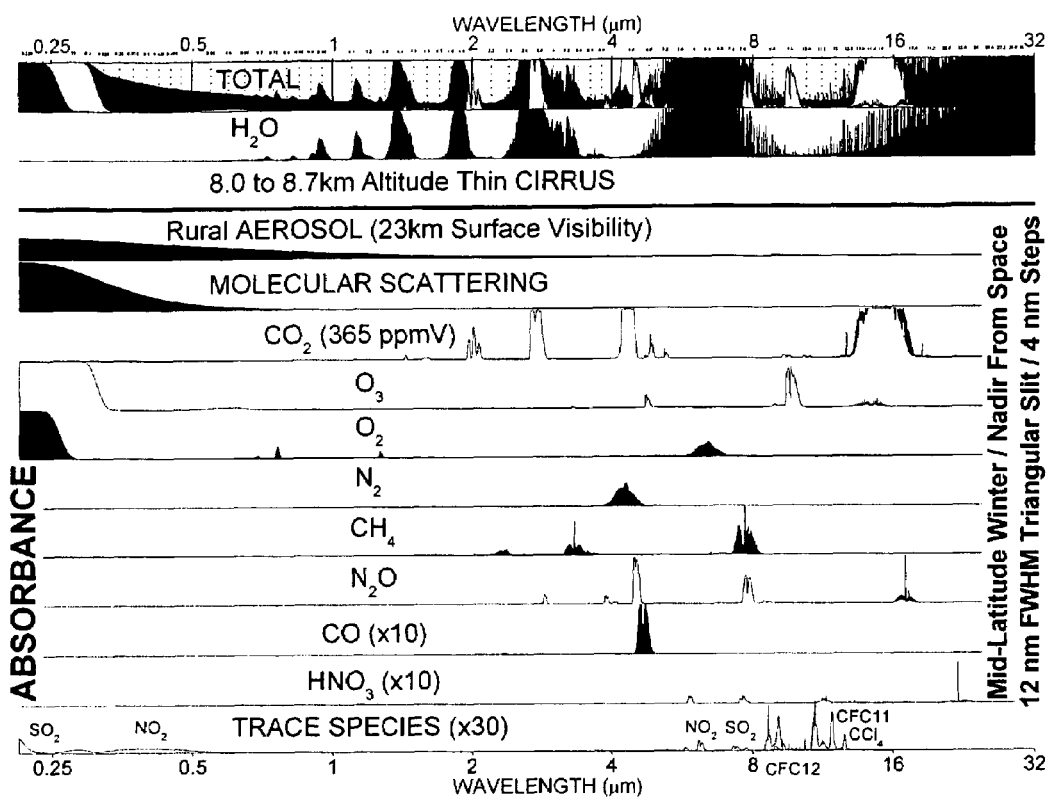
FIG. 1 is a plot of spectral absorbance for the primary sources of atmospheric extinction. These 4 nm resolution curves were generated by an embodiment of the invention for a vertical path from space with a mid-latitude winter model atmosphere.

This approximation works well for a number of reasons. As illustrated in FIG. 1, a single molecular species serves as a dominant absorption source in much of the visible through IR spectral region. Where overlap between molecular species does occur, H$_2$O is typically one of the species; since H$_2$O is an asymmetry top, its transition frequency and line strength distributions are well represented as random. It is therefore quite reasonable to approximate H$_2$O absorption correlation with other molecular species as random. Furthermore, when moderate spectral resolution results are sought, spectral averaging of the relatively fine resolution MODTRAN™ values tends to stochastically cancel statistical variations if there is no overall biasing.

Within MODTRAN™, the individual species spectral bin transmittance is itself partitioned into three distinct components. These components are:

(1) Line center transmittance: the transmittance arising from molecular transitions centered within the spectral bin;

(2) Line tail transmittance: the transmittance arising from molecular transitions centered outside of the spectral bin but not further than 25 cm$^{-1}$ from the spectral bin center; and (3) Continuum transmittance: the transmittance arising from molecular transitions centered more than 25 cm$^{-1}$ from a spectral bin.

Again, the assumption is made that these terms are randomly correlated:

$$\langle t^{k\_abs} \rangle = \langle t^{k\_cen} \rangle \langle t^{k\_tail} \rangle \langle t^{k\_cont} \rangle. \quad (20)$$

Since the line tail and continuum contributions tend to be relatively smoothly varying across the spectral interval, the random correlation assumption is quite reasonable. In the following subsections, the modeling approach for each of these components is detailed. Additional sections describe treatment of auxiliary species and of aerosols for which spectral optical properties vary with altitude.

Line Center Transmittance

The starting point for the calculation of the MODTRAN™ in-band molecular line center transmittance is the Plass expression. Plass proved that the homogeneous path transmittance resulting from n identical molecular lines randomly distributed within each spectral interval of width $\Delta v$ for a contiguous collection of spectral bins is given by the following power law expression:

$$\langle t^{k\_cen} \rangle = \left(1 - \frac{W^{sl}}{\Delta v}\right)^n, \quad (21)$$

where $W^{sl}$ is the finite-bin equivalent width (EW) of a single Voigt line, $$W^{sl}(Su, \gamma_c, \gamma_d) \equiv \int_{\Delta v} [1 - \exp(-Suf_v)] dv; \quad (22)$$

$$f_v(\gamma_c, \gamma_d) \equiv \frac{\gamma_c}{\pi^{3/2}} \int_{-\infty}^{\infty} \frac{\exp(-x^2)}{\gamma_c^2 + (v - \gamma_d x)^2} dx.$$

The Voigt spectral line-shape $f_v(\gamma_c,\gamma_d)$ [cm] at line center displacement frequency v, the convolution of Lorentz and Doppler line-shape functions, characterizes the spectral dependence of molecular line absorption. In these equations, $\gamma_c$ is a collision (Lorentz) half-width at half maximum [cm$^{-1}$], $\gamma_d$ is a Doppler half-width at 1/e of the maximum [cm$^{-1}$], S is a line strength [cm$^{-2}$/Atm] and u is a path column density [Atm cm].

The Plass expression, Eq. (21), defines the band model curve-of-growth (COG) for the randomly distributed collection of identical molecular lines, i.e., the rate at which the molecular absorption increases with column density. The actual distribution of molecular lines in a specific spectral interval will exhibit a COG unique to the spectral band. The objective of band model theory in general is to find an optimal fit to each COG. In MODTRAN™, the Plass expression is used as the COG functional form. The fitting parameters are the average line strength of each line S, the effective number of molecular lines in the spectral interval n, the spectral bin averaged Lorentz half-width $\gamma_c$ and the Doppler half-width $\gamma_d$.

Band Model Parameter Determination

The traditional band model equations for the temperature dependent line strength, S(T), and effective line number, n(T), parameters are derived by fitting the EW COG in the weak-line (small column density) and Lorentz strong-line (large column density) limits. The Voigt EW varies linearly with column density in the weak-line limit, and it increases with the square root of the column density in the strong line limit. The accuracy of the interpolation between these limits largely dictates the accuracy of the band model. The expressions for the band model parameters resulting from the weak and strong line limit constraints are:

$$S(T) = \frac{1}{n(T)} \sum_{sub-bin\ j} S_j(T); n(T) = \frac{1}{\sqrt{S(T)}} \sum_{sub-bin\ j} \sqrt{S_j(T)}. \quad (23)$$

(Note that the actual temperature dependent parameters stored by MODTRAN™ are (S/d)≡nS/$\Delta v$ and (1/d)≡n/$\Delta v$.) Typically, these sums would be over all the transitions centered within the spectral bin for a given molecular species. For MODTRAN™, the spectral bin sums are over spectral sub-intervals of width 0.01 cm$^{-1}$, and each $S_j(T)$ is itself the sum of temperature-dependent line strengths for lines centered in sub-interval j. This coagulation of molecular transitions within narrow spectral bins has no effect on the calculation the total line strength, n(T) S(T), but it reduces the effective number of lines, n(T). MODTRAN™ temperature dependent band model parameters are generated for 6 atmospheric temperatures, T=180, 205, 230, 255, 280, and 305K. The Lorentz half-width band model parameter, $\gamma_c^0$, is computed as a line strength weighted average of molecular transition half-widths at standard temperature ($T_0$=273.15K) and pressure ($P_0$=1 Atm).

$$\gamma_c^0 = \frac{\sum_p \gamma_{c,p}^0 S_p}{n(T_0) S(T_0)}; \gamma_c(P, T) = \gamma_c^0 \left(\frac{P}{P_0}\right) \left(\frac{T_0}{T}\right)^{3/4}. \quad (24)$$

The Doppler half-width at 1/e of maximum is defined using the spectral bin center frequency, $\bar{v}$:

$$\gamma_d = \sqrt{2kT/m\bar{v}}/c, \quad (25)$$

where k is the Boltzmann constant (1.3807E-16 erg/K), m is the molecular mass (g/molecule), and c is the speed of light in a vacuum (2.9979246E+10 cm/sec).

Sub-intervals are used in the definition of the band model parameters, Eq. (23), for two reasons: (1) the atmospheric absorption from nearly coincident lines (such as those arising from degenerate transitions) is accurately modeled as a single line of combined strength, and (2) the Plass expression was derived for a random distribution of line centers, but near degeneracy occurs at a higher frequency than a random distribution would predict. On a more practical level, it has been shown by extensive comparisons to LBL calculations that the classical expression for the effective number of lines n is too large; too much absorption is predicted. The sub-interval summing decreases the effective line number without changing the total line strength nS, and thereby lowers the band model absorption.

To increase accuracy in the IMPROVEMENTS TO MODTRAN4™ band model absorption for the coarser resolution band models ($\Delta v$=1.0, 5.0 and 15.0 cm$^{-1}$), the effective line number band model parameter is tuned using the 0.1 cm$^{-1}$ band model. The two-step approach is relatively straightforward. First, the column amount U is determined for which the 0.1 cm$^{-1}$ band model predicts a homogeneous path transmittance equal to 1/e when integrated (summed) over a given coarse spectral bin:

$$\frac{1}{N} \sum_{N \, bias} \langle t^{k\_abs}(U) \rangle_{0.1 \text{cm}^{-1}} = \frac{1}{e}; N = \frac{\Delta v}{0.1 \text{ cm}^{-1}}. \quad (26)$$

Here $\Delta v$ is the coarse band model bin width and the loop is over the N 0.1 cm$^{-1}$ spectral sub-bins within the coarse spectral bin. Once the spectrally dependent 1/e transmittance column density has been determined, the coarse resolution effective line number n is perturbed to give the same in-band transmittance:

$$\langle t^{k\_abs}(U;n) \rangle_{\Delta v} = 1/e. \quad (27)$$

These calculations are performed at each of the MODTRAN™ temperatures and for a specific pressure depending upon the molecule. For H$_2$O, which is concentrated near the ground, the reference pressure is set to 1 Atm. The absorption of O$_3$ is most important at higher altitudes, so its effective line number values are tuned for a pressure of 0.1 Atm. For all other species, the homogeneous path is defined with a reference pressure of 0.5 Atm.

Calculation of Equivalent Width

The precise spectral domain of the finite bin EW integral in Eq. (22) was left ambiguous. In traditional band model theory, the finite bin EW is computed for a line located in the center of the spectral bin; thus, the spectral domain of the integral extends from $-\Delta v/2$ to $+\Delta v/2$. However, MODTRAN™ seeks to determine the EW of lines whose centers are randomly distributed within the spectral bin. For a single pure Lorentzian line in the weak line limit, the exact expression for the offset from bin center $D(r_c)$ that produces a finite bin integrated absorption equal to the random distribution value can be derived as a function of the ratio of the Lorentz half-width to the bin width, $r_c = \gamma_c/\Delta v$:

$$\left(\frac{D(r_c)}{\Delta v}\right)^2 = \frac{1}{4} - (1 + r_c^2) \frac{1 - r_c \tan\left[r_c \ln\left(1 + \frac{1}{r_c^2}\right)\right]}{2 + \left(\frac{1 - r_c^2}{r_c}\right) \tan\left[r_c \ln\left(1 + \frac{1}{r_c^2}\right)\right]}. \quad (28)$$

The function $D(r_c)$ is monotonic for positive $r_c$, decreasing from $D(0) = \frac{1}{2}\Delta v$ (the edge of the spectral bin) to $D(r_c \to \infty) = \Delta v/\sqrt{12}$. The terrestrial surface Lorentz half-widths are typically ~0.07 cm$^{-1}$. For the MODTRAN™ band model widths of 0.1, 1.0, 5.0 and 15.0 cm$^{-1}$, the 0.07 cm$^{-1}$ Lorentz transition weak-line displacement values are D(0.07/0.1)=0.028 cm$^{-1}$, D(0.07/1.0)=0.34 cm$^{-1}$, D(0.07/5.0)=1.96 cm$^{-1}$, and D(0.07/15.0)=6.2 cm$^{-1}$, respectively.

The weak-line Lorentz transition offsets are only a guide for determining the optimal Voigt line-shape transition values; the actual displacements used in MODTRAN™ are D[0.1 cm$^{-1}$]=0.025 cm$^{-1}$, D[1.0 cm$^{-1}$]=0.30 cm$^{-1}$, D[5.0 cm$^{-1}$]=1.97 cm$^{-1}$, and D[15.0 cm$^{-1}$]=6.3 cm$^{-1}$ with the EW integral having the form:

$$W^{sl} = \int_{-1/2\Delta v + D}^{1/2\Delta v + D} (1 - e^{-Suf_v}) dv \quad (29)$$

$$= \int_0^{1/2\Delta v - D} (1 - e^{-Suf_v}) dv + \int_0^{1/2\Delta v + D} (1 - e^{-Suf_v}) dv$$

-continued $$= 2 \int_0^{\infty} (1 - e^{-Suf_v}) dv - \int_{1/2\Delta v - D}^{\infty} (1 - e^{-Suf_v}) dv -$$

$$\int_{1/2\Delta v + D}^{\infty} (1 - e^{-Suf_v}) dv$$

$$\equiv 2 W_0 - W_{1/2\Delta v - D} - W_{1/2\Delta v + D}$$

The second line above is derived by noting that $f_v$ is symmetric in spectral displacement frequency $v(f_v = f_{-v})$, and the Voigt line tail EW $W_\Delta$ is defined in the last line. The methodology employed to compute the Voigt line tail EW is described in the parent SERTRAN patent application, incorporated by reference herein.

Spherical Refractive Geometry

From its inception, MODTRAN™ included a spherical refractive geometry package. The modeling of refraction was introduced to model near-horizon sun and/or low-altitude near-horizontal path scenarios. As is well known, the sun is already below the horizon when sunset begins. The sun only appears as if it is above the horizon because of refraction.

With the locally spherical Earth approximation used in MODTRAN™, Snell's Law dictates that the product of three terms, (1) the index of refraction, $1 + N_{\bar{v}}(H_s)$, (2) the Earth center distance (the sum of the Earth radius $R_e$ and the altitude $H_s$), and (3) the sine of the path zenith angle $\sqrt{1 - \mu_s^2}$ at each position s along a line-of-sight (LOS), is a path constant:

$$[1 + N_{\bar{v}}(H_s)](R_e + H_s)\sqrt{1 - \mu_s^2} = \text{Constant} \quad (32)$$

Here, $\mu_s$ is the cosine of the path zenith at path length s. The MODTRAN™ refractivity, $N_{\bar{v}}$, vertical profile is computed at the mean spectral frequency $\bar{v}$ of the calculation band pass and is defined as a function of pressure, temperature, H$_2$O density, CO$_2$ density and the central frequency.

For a path specified by an initial altitude $H_0$ and direction $\mu_0 < 0$, MODTRAN™ follows the line-of-sight (LOS) trajectory through the atmosphere continually updating the path zenith angle according to Eq. (1). With normal refraction, the path bends downward from the straight-line path because of the decrease in refractivity with increasing altitude. A limb path is defined as a downward LOS which passes through a minimum tangent altitude, $H_{tan}$, before beginning an upward trajectory. At the tangent altitude, the path zenith angle is exactly 90°:

$$[1 + N_{\bar{v}}(H_0)](R_e + H_0)\sqrt{1 - \mu_0^2} = [1 + N_{\bar{v}}(H_{tan})](R_e + H_{tan}). \quad (33)$$

The MODTRAN™ refractive geometry package was specifically designed to model this scenario.

When large temperature and/or H$_2$O gradients are present within the atmosphere, non-standard refraction can occur. For optical frequencies, this scenario can arise within the marine boundary layer. If refractivity gradient, $dN_{\bar{v}}/dz$, is positive at altitude $z_s$ along the optical path, subrefraction, i.e., upward bending of the optical path, occurs. On the other hand, if the decrease in refractivity with altitude is excessive, superrefraction results. Superrefraction is defined as larger than normal bending towards the Earth. If the radius of curvature for the refraction in an upward path exceeds the radius of curvature of the Earth, the path will pass through a tangent maximum and proceed back downward towards the Earth. The MODTRAN™ refractive geometry package was not designed to handle either of these scenarios. In particular, an upward path is always assumed to continue upward; if the superrefraction exceeds the critical refractivity gradient, the sine of the path zenith angle will exceed one at the boundary layer altitude level just above the tangent maximum. IMPROVEMENTS TO MODTRAN4™ detects this failure, and aborts processing.

To properly model the subrefraction and superrefraction scenarios, the invention (IMPROVEMENTS TO MODTRAN4™) provides an option to bypass the built-in refractive geometry package and explicitly enter refractive path data. Specification of a user-defined path requires that some stringent rules be followed. Four columns of data are required. As illustrated in Table 1 (This example is kindly been provided by Drs. Denis Dion and Vincent Ross, Defence Research and Development Canada, Valcartier, 2005), these columns contain the cumulative (spherical) Earth surface distance in meters, the altitude in meters, the path zenith angle in degrees, and the incremental path segment length in meters. In Table 1, all lines beginning with an exclamation are ignored and the word "NEXT" is used as the delimiter. Every atmospheric profile altitude level between the beginning of the path (H1) and the end of the path (H2) must be explicitly included in the user-defined path file. If the LOS passes through a minimum tangent point, the altitude of the tangent point and the altitude of the minimum of H1 and H2 must be included in the path definition. Similarly, if the LOS passes through a maximum tangent point, the altitude of the tangent point and the altitude of the maximum of H1 and H2 must be included in the path definition. In Table 1, a minimum tangent altitude occurs at 0.16075426526368 m, and the final altitude (H2=25.821244410585 m) is listed as the third entry in the downward leg. If a MODTRAN™ atmosphere includes a non-zero ground altitude or a cloud, it is best to run MODTRAN™ first without a user-defined path to determine the model relayering. Note that it is not necessary that "mirrored" path segments within a common atmospheric layer have identical path lengths or angles.

TABLE 1

Sample User-Defined Path Parameter File.

!#Full refraction (Mirage ray)
!#Curved earth representation (R = 6371230.0 m)
!

| !Earth surface !distance (m) | Altitude (m) | Zenith Angle (deg) | Segment Lengths (m) |
|---|---|---|---|
| ! | | | |
| 0.0000000000000 | 29.900000000000 | 90.189000000000 | 0.0000000000000 |
| 1041.9012954644 | 26.538244292473 | 90.180733953598 | 1041.9113336288 |
| 1270.3560625281 | 25.821244410585 | 90.178908112818 | 228.45683147277 |
| 2038.7644494551 | 23.463065803670 | 90.172762325063 | 768.41497742361 |
| 2964.7678300263 | 20.731295125158 | 90.165288500462 | 926.01062164312 |
| 3824.1902900742 | 18.304583613239 | 90.158276863904 | 859.42851892983 |
| 4621.1260668439 | 16.148865050039 | 90.151693040154 | 796.94084715816 |
| 5359.4938828508 | 14.233877421347 | 90.145503806883 | 738.37205984105 |
| 6043.0445474172 | 12.532738097948 | 90.139677023359 | 683.55421721182 |
| 6675.3673650761 | 11.021566456806 | 90.134181491957 | 632.32579225008 |
| 7259.8955694608 | 9.6791486444739 | 90.128986871664 | 584.53069546048 |
| 7799.9109567221 | 8.4866397766488 | 90.124063541044 | 540.01747381047 |
| 8298.5481454158 | 7.4272993933662 | 90.119382401136 | 498.63893670373 |
| 8758.7986010627 | 6.4862564561342 | 90.114914739278 | 460.25192023864 |
| 9183.5148066126 | 5.6503005880400 | 90.110631911152 | 424.71743276353 |
| 9575.4155575907 | 4.9076966262520 | 90.106504727038 | 391.90177926706 |
| 9937.0915791127 | 4.2480198836023 | 90.102503543286 | 361.67688300182 |
| 10271.013265885 | 3.6620098066495 | 90.098596673395 | 333.92240826494 |
| 10579.540504055 | 3.1414399758701 | 90.094750408679 | 308.52784207464 |
| 10864.936400155 | 2.6790026230402 | 90.090926277237 | 285.39640111885 |
| 11129.386251322 | 2.2682060446596 | 90.087080169216 | 264.45027291130 |
| 11375.024382517 | 1.9032834713067 | 90.083158113572 | 245.63848268456 |
| 11603.982028179 | 1.5791121136302 | 90.079087071713 | 228.95793773649 |
| 11818.455868850 | 1.2911412485443 | 90.074773233897 | 214.47408232363 |
| 12020.841683321 | 1.0353283360997 | 90.070068860443 | 202.38601311481 |
| 12214.001067940 | .80808227023856 | 90.064744519726 | 193.15954626868 |
| 12401.895848521 | .60621296678608 | 90.058369650734 | 187.89490992932 |
| 12591.541884888 | .42688658099378 | 90.049986342712 | 189.64613663414 |
| 12802.014760646 | .26758572597844 | 90.036744693052 | 210.47294785778 |
| 13135.178041776 | .16075426526368 | 90.000000000000 | 333.16331427414 |
| 13468.341309379 | .26758572597844 | 89.963255306948 | 333.16330074681 |
| 13678.814177420 | .42688658099378 | 89.950013657288 | 210.47294014061 |
| 13868.460213787 | .60621296678608 | 89.941630349266 | 189.64613663414 |
| 14056.354994368 | .80808227023856 | 89.935255480274 | 187.89490992932 |
| 14249.514378987 | 1.0353283360997 | 89.929931139557 | 193.15954626868 |
| 14451.900193458 | 1.2911412485443 | 89.925226766103 | 202.38601311481 |
| 14666.374034128 | 1.5791121136302 | 89.920912928287 | 214.47408232363 |
| 14895.331679791 | 1.9032834713067 | 89.916841886428 | 228.95793773649 |
| 15140.969810986 | 2.2682060446596 | 89.912919830784 | 245.63848268456 |
| 15405.419662153 | 2.6790026230402 | 89.909073722763 | 264.45027291130 |
| 15690.815558253 | 3.1414399758701 | 89.905249591321 | 285.39640111885 |
| 15999.342796423 | 3.6620098066495 | 89.901403326605 | 308.52784207464 |
| 16333.264483195 | 4.2480198836023 | 89.897496456714 | 333.92240826494 |
| 16694.940504717 | 4.9076966262520 | 89.893495272962 | 361.67688300182 |
| 17086.841255695 | 5.6503005880400 | 89.889368088848 | 391.90177926706 |
| 17511.557461466 | 6.4862564561342 | 89.885085260722 | 424.71743298422 |

TABLE 1-continued

Sample User-Defined Path Parameter File.

!#Full refraction (Mirage ray)
!#Curved earth representation (R = 6371230.0 m)
!

| !Earth surface<br>!distance (m) | Altitude<br>(m) | Zenith Angle<br>(deg) | Segment Lengths<br>(m) |
|---|---|---|---|
| 17971.807917113 | 7.4272993933662 | 89.880617598864 | 460.25192023864 |
| 18470.445105806 | 8.4866397766488 | 89.875936458956 | 498.63893670373 |
| 19010.460493068 | 9.6791486444739 | 89.871013128336 | 540.01747381047 |
| 19594.988697452 | 11.021566456806 | 89.865818508043 | 584.53069546048 |
| 20227.311515111 | 12.532738097948 | 89.860322976641 | 632.32579225008 |
| 20910.862179678 | 14.233877421347 | 89.854496193117 | 683.55421721182 |
| 21649.229995685 | 16.148865050039 | 89.848306959846 | 738.37205984105 |
| 22446.165772454 | 18.304583613239 | 89.841723136096 | 796.94084715816 |
| 23305.588232502 | 20.731295125158 | 89.834711499538 | 859.42851892984 |
| 24231.591613073 | 23.463065803670 | 89.827237674937 | 926.01062164312 |
| 25000.000000000 | 25.821244410585 | 89.821091887182 | 768.41497742361 |

NEXT

The full suite of refractive path input requirements do make the use of the user-specified refractive geometry option rather complex, but this is currently necessary for modeling strong index of refraction gradients such as those observed in the marine boundary layer.

Inhomogeneous Paths

This line center transmittance section began with a description of the Plass expression for the transmittance of a homogeneous path and the use of this expression by MODTRAN™ to estimate line center transmittances as a function of both column density and the temperature and pressure dependent band model parameters (pressure for the Lorentz half-width). However, the molecular transmittances of the band model RTE, Eq. (13), are defined for an inhomogeneous path. More specifically, the molecular spectral cross-sections $\kappa_{v,i}^{abs}(s)$ and molecular densities $n_i(s)$ are functions of path length s along the line-of-sight, and atmospheric conditions change as the path is traversed. In MODTRAN™, this disconnect is rectified by modeling the Earth atmosphere as stratified, with molecular and particulate densities, total pressure, and ambient temperature defined as a function of altitude (there is an option in MODTRAN™ to alternatively define temperature and density profiles as a function of pressure with altitudes determined from the hydrostatic equation and a user defined ground altitude). The layering is assumed to be relatively finely gridded, so that a homogeneous path can be defined within individual layers.

Implementation of the IMPROVEMENTS TO MODTRAN4™ user-specified refractive geometry option required that a completely new approach for calculating MODTRAN™ column densities be incorporated into the model. In MODTRAN4™, column density calculations are performed coincident with the refractive geometry calculation; as the refractive path is incremented in small steps, ds, and the cosine of the path zenith is updated, column amounts are summed by modeling the short incremental segments as a straight lines. With the user-specified refractive geometry option, the full path length within a layer is provided, but not the detailed mapping of path length as a function of altitude within the layer. Like earlier MODTRAN™ versions, IMPROVEMENTS TO MODTRAN4™ assumes an exponential variation of densities and pressure vertically between altitude levels and a linear variation of temperature vertically between altitude levels. However, IMPROVEMENTS TO MODTRAN4™ also models the refracted path between altitude levels as a circular arc, typically with an extremely large radius of curvature—much larger than the Earth radius for normal refraction:

$$u_\sigma = \rho_{l_\sigma} \int_{s_{\sigma-1}}^{s_\sigma} (\rho_{l_\sigma - 1}/\rho_{l_\sigma})^{h_\sigma(s)} ds \quad (34)$$

$$\overline{P_\sigma} = \frac{\rho_{l_\sigma}^{air} P_{l_\sigma}}{u_\sigma^{air}} \int_{s_{\sigma-1}}^{s_\sigma} \left(\frac{\rho_{l_\sigma-1}^{air} P_{l_\sigma-1}}{\rho_{l_\sigma}^{air} P_{l_\sigma}}\right)^{h_\sigma(s)} ds;$$

$$h_\sigma(s) \equiv \frac{H(s) - H_{l_\sigma}}{H_{l_\sigma-1} - H_{l_\sigma}}$$

$$\overline{T_\sigma} = \frac{\rho_{l_\sigma}^{air}}{u_\sigma^{air}} \int_{s_{\sigma-1}}^{s_\sigma} \left(\frac{\rho_{l_\sigma-1}^{air}}{\rho_{l_\sigma}^{air}}\right)^{h_\sigma(s)} [T_{l_\sigma} + h_\sigma(s)(T_{l_\sigma-1} - T_{l_\sigma})] ds$$

In these path integrals, s is the path length variable; $s_{\sigma-1}$ and $s_\sigma$ are path lengths to the beginning and end of segment σ, H(s) is the altitude at path length s; $l_\sigma$ is index of the vertical layer containing segment σ, $H_{l_\sigma}$, $\rho_{l_\sigma}$, $P_{l_\sigma}$ and $T_{l_\sigma}$ are the altitude, density, pressure and temperature at the bottom of vertical layer $l_\sigma$; and $H_{l_\sigma-1}$, $\rho_{l_\sigma-1}$, $P_{l_\sigma-1}$ and $T_{l_\sigma-1}$ are the same quantities but at the top of vertical layer $l_\sigma$.

If Beer's Law were applicable, the LOS molecular line center transmittance could be computed by simply stringing together individual segment transmittances for each species. However, as detailed above, the in-band absorption does not retain a linear dependence on column density as that density increases. The Curtis-Godson (CG) approximation provides a solution to the band model inhomogeneous path problem. The approach involves approximating the inhomogeneous path by a quasi-equivalent homogeneous path. First, a total path in-band weak-line optical depth $(\tau^{cen})_{\overline{v}}^{weak-line}$ for the band centered at $\overline{v}$ is computed:

$$(\tau^{cen})_{\overline{v}}^{weak-line} \equiv \sum_{\sigma\,segments} n(\overline{T_\sigma}) S(\overline{T_\sigma}) u_\sigma \quad (35)$$

$$= \sum_{\sigma\,segments} \left[\sum_l S_l(\overline{T_\sigma})\right] u_\sigma.$$

This value is used to normalized a CG path-averaged effective line number, $\bar{n}$ $$\bar{n} \equiv \frac{\sum_{\sigma\ segments}[n(\overline{T_\sigma})S(\overline{T_\sigma})u_\sigma]n(\overline{T_\sigma})}{(\tau^{cen})_\nu^{weak-line}} \quad (36)$$

The CG single-line optical depth parameter $\overline{Su}$ is defined as total path in-band weak-line optical depth normalized by the number of lines:

$$\overline{Su} \equiv \frac{(\tau^{cen})_\nu^{weak-line}}{\bar{n}} \quad (37)$$

Finally, the CG Lorentz and Doppler line-width parameters are defined as the optical depth weighted sum of the n line widths in each band normalized by the product of the weak-line optical depth and the CG effective line number:

$$\bar{\gamma} \equiv \frac{\sum_{\sigma\ segments}[n(\overline{T_\sigma})S(\overline{T_\sigma})u_\sigma]n(\overline{T_\sigma})\gamma(\overline{T_\sigma},\overline{P_\sigma})}{(\tau^{cen})_\nu^{weak-line}\bar{n}} \quad (38)$$

In MODTRAN™, the CG data is inserted into the Plass expression to compute line center transmittance for the multi-segmented paths.

$$\langle t^{k\_cen}\rangle^{inhomogeneous\ path} = \left(1 - \frac{W^{st}(\overline{Su},\gamma_c,\gamma_d)}{\Delta\nu}\right)^n. \quad (39)$$

The CG approximation works well when the bulk of the absorption occurs within a sub-section of the LOS over which the line shape function does not vary drastically. For most ambient atmospheric species, this condition is satisfied independent of the particular LOS. An important exception for the terrestrial atmosphere is ozone. The absolute $O_3$ concentration has a relatively constant profile from the Earth's surface up into the stratosphere. However, the character of Voigt line shape changes from Lorentzian to Doppler over this altitude range. Thus, MODTRAN™ models the $O_3$ in-band absorption with a higher-order CG correction.

Figure 2:
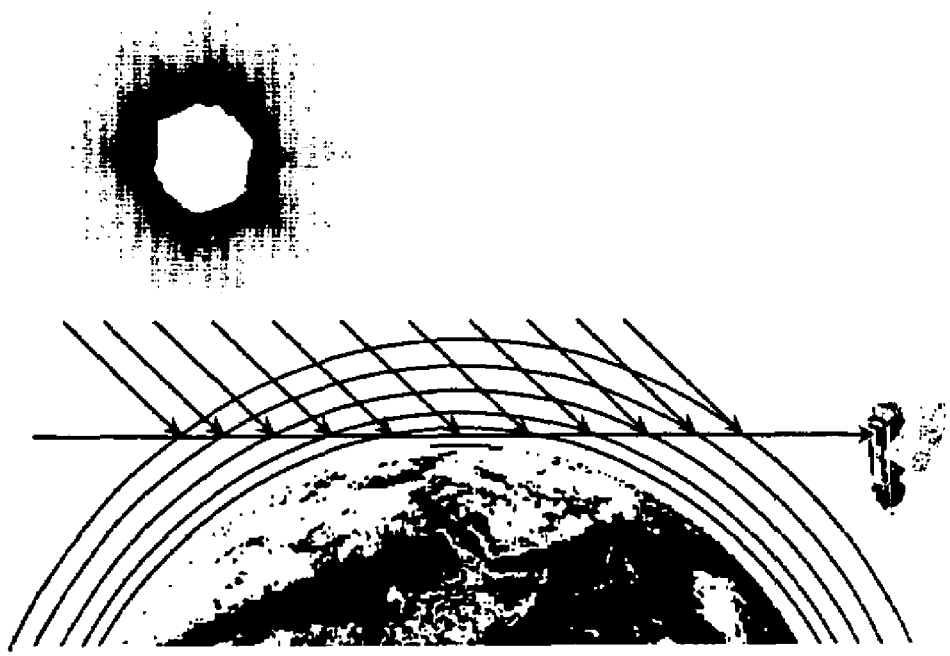
FIG. 2 is an illustration of LOS and solar illumination paths, useful in understanding an aspect of the invention.

Applying CG path averaging for each of the solar illumination paths arising in the spherical Earth single scatter solar calculation was deemed computationally too expensive when these calculations were introduced into MODTRAN™. As illustrated in FIG. 2, CG averages can be computed incrementally for the direct LOS as the calculation traverses outward along the path from the sensor; however, the LOS level intersection to sun paths are each independent because of the Earth's curvature, even with horizontal homogeneity of the spherical shell layering. To simplify the solar illumination calculations, MODTRAN™ approximates the illumination path at each LOS altitude level intersection (and the tangent point) as a single homogeneous segment using cumulative column densities and species-dependent effective temperatures and pressures:

$$\overline{P_s^k} = \sum_{\substack{\sigma\ segments\\s\ to\ sum}} u_\sigma^k \overline{P_\sigma} \bigg/ \sum_{\substack{\sigma\ segments\\s\ to\ sum}} u_\sigma^k \quad (40)$$

$$\overline{T_s^k} = \sum_{\substack{\sigma\ segments\\s\ to\ sum}} u_\sigma^k \overline{T_\sigma} \bigg/ \sum_{\substack{\sigma\ segments\\s\ to\ sum}} u_\sigma^k$$

These single illumination path layers are then coupled to the LOS using CG path averaging to calculate the L-shaped path transmittances.

Line Tail Transmittance

The MODTRAN™ spectral bin line tail transmittance is the attenuation arising from molecular transitions centered outside of the bin but no more than 25 $cm^{-1}$ from the bin center. Unlike the line center spectral attenuation, the line tail absorption varies smoothly across each spectral bin with at most a single minimum. Thus, the entire line tail spectral absorption cross-section curve can be accurately fit to temperature and pressure dependent Padé approximants. This fitting procedure is described in detail within the parent patent application.

For the IMPROVEMENTS TO MODTRAN4™ invention, the Padé parameter database is generated at pressures of 1.0 and 0.1 Atm and at the 6 evenly spaced MODTRAN™ temperatures between 180 and 305K. The Padé parameter interpolations are linear in temperature and linear in pressure-squared. The $P^2$ dependence arises because of the $\gamma_c^2$ term in the denominator of the Voigt line-shape, Eq. (22).

An IMPROVEMENTS TO MODTRAN4™ parameter defines the number of monochromatic line tail absorption cross-section calculations per spectral bin so the line tails can be computed at arbitrarily fine spectral resolution. Nominally, the parameter is set to 5. The monochromatic line tail optical depths are added for multiple segment paths since Beer's Law applies, and these summed optical depths are modeled as varying linearly between spectral points for computing the in-band line tail transmittances.

Line Continuum Transmittance

The primary atmospheric molecules for which lines tails beyond 25 $cm^{-1}$ from line center sum to make a significant contribution to atmospheric absorption are $H_2O$ and $CO_2$. MODTRAN™ adopts the continuum algorithms employed in standard LBL models for both of these molecules.

The temperature dependent $H_2O$ continuum spectral absorption cross-section $\kappa_\nu^{H_2O\ cont}(T)$ is partitioned into a foreign and a temperature-dependent self-broadened component:

$$\kappa_\nu^{H_2O\ cont} = \nu\ \tanh\left(\frac{c_2\nu}{2T}\right) \times \quad (44)$$

$$\left\{\left(\frac{P_{total}-P_{H_2O}}{P_{total}}\right)C_\nu^{H_2O\ foreign}(296K) + \left(\frac{P_{H_2O}}{P_{total}}\right)\left[\left(\frac{T-260K}{36K}\right)\right.\right.$$

$$\left.\left.C_\nu^{H_2O\ self}(296K) + \left(\frac{296K-T}{36K}\right)C_\nu^{H_2O\ self}(260K)\right]\right\}$$

The spectral foreign ($C_\nu^{H_2O\ foreign}$) and self ($C_\nu^{H_2O\ self}$) broadened $H_2O$ continuum parameters [($cm^2$/mol)/$cm^{-1}$] are tabulated from 0 to 10,000 $cm^{-1}$ on a 5 $cm^{-1}$ grid; the self-broadened term endpoint values are used for temperatures below 260K or above 296K rather than extrapolation. The $H_2O$ continuum data in MODTRAN™ are CKD 2.4, i.e. Version 2.4 of the Clough-Kneizys Data.

The form of the $CO_2$ continuum spectral absorption cross-section is simpler than that of $H_2O$. $CO_2$ has a zero dipole moment, so partitioning into foreign and self broadened components is unnecessary:

$$\kappa_\nu^{CO_2\ cont}(T) = \nu\ \tanh\left(\frac{c_2\nu}{2T}\right)C_\nu^{CO_2} \quad (45)$$

The $CO_2$ data is tabulated on a 10 $cm^{-1}$ grid from 0 to 10,000 $cm^{-1}$. Since the $CO_2$ continuum cross-section values are themselves not functions of mole fraction, they can and are directly incorporated into the $CO_2$ line tail band model parameters.

Auxiliary Species

All versions of MODTRAN™ compute the absorption and emission resulting from a standard set of atmospheric molecules. For MODTRAN4™, this standard set includes 26 molecules. However, the invention (IMPROVEMENTS TO MODTRAN4™) provides a new auxiliary species option which couples an arbitrary number of additional molecular species into MODTRAN's radiation transport. These molecules can be modeled either as Beer's Law absorption cross-section species or via the IMPROVEMENTS TO MODTRAN4™ band model. The band model provides greater accuracy if optical depths are substantial, while cross-section data is generally more readily available. The IMPROVEMENTS TO MODTRAN4™ database includes band model parameter data for 24 HITRAN species (OH, HF, HCl, HBr, HI, ClO, OCS, $H_2CO$, HOCl, $N_2$, HCN, $CH_3Cl$, $H_2O_2$, $C_2H_2$, $C_2H_6$, $PH_3$, $COF_2$, $H_2S$, HCOOH, $HO_2$, O, $NO^+$, HOBr and $C_2H_4$) not among the MODTRAN™ set of standard molecules (actually, $N_2$ is one of the MODTRAN™ standard atmospheric molecules, but it is modeled in MODTRAN™ as a cross-section species, not as a band model molecule).

In the IMPROVEMENTS TO MODTRAN4™ invention, auxiliary species molecular densities can be defined via user-specified atmospheric vertical profiles or with 'default' model profiles; currently, profiles are provided for 16 of the new band model species (OH through $PH_3$ in the above list). The molecular species temperature-dependent optical data inputs must conform to MODTRAN™ definitions. Thus, if molecular band model data are user-supplied, this data must be defined in accordance with the MODTRAN™ band model formalism [Eqs. (23), (24) and (41)]; similarly, molecular absorption cross-section data must be defined at the 6 MODTRAN™ temperatures (180, 205, 230, 255, 280 and 305K) and in units of $cm^2$/molecule.

The mechanism for introducing auxiliary species is similar to that for MODTRAN™ standard atmospheric molecular species when user-defined profiles or radiosonde data are being entered. For each atmospheric altitude profile level, the density of each absorption species is specified. Unlike the standard molecules, the number of auxiliary species is read from the profile table header. This number is a TOTAL number of auxiliary species in the user's master list. The input to the IMPROVEMENTS TO MODTRAN4™ invention accepts a negative sign "−" prefix for any species name to indicate the species is to be excluded from the current calculation. This input format was instituted to avoid having to completely reconfigure an input stream each time a species is added or removed. A star (*) at the end of species name indicates band model rather than absorption cross-section data is to be used. The optical data for each species is stored in species-dependent auxiliary input files (SF6.BM for a $SF_6$ absorption cross-section data file, SF6.cBM for a $SF_6$ line center band model data file, and SF6.tBM for a $SF_6$ line tail band model data file).

Figure 3:
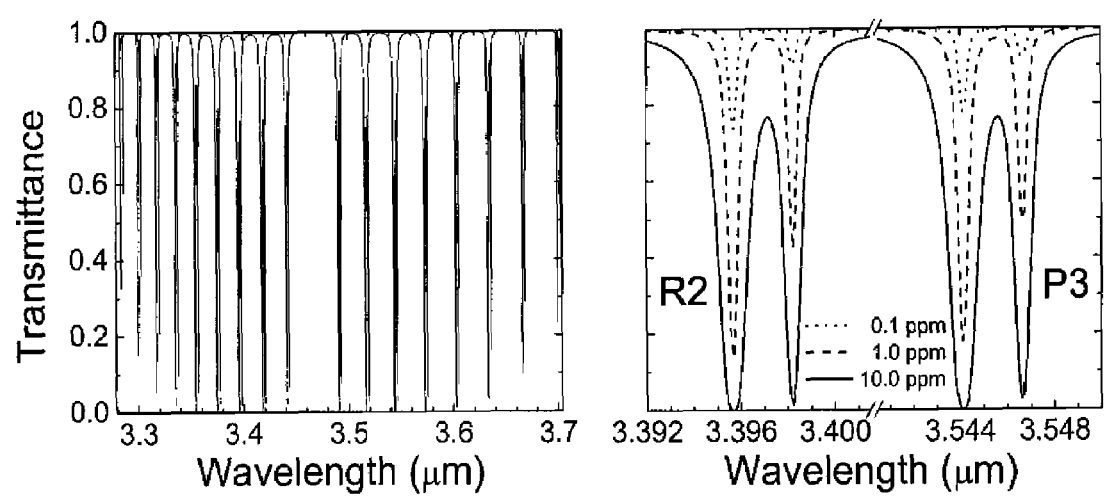
FIG. 3 is two plots illustrating the auxiliary species aspect of the invention. These are Isolated HCl Nadir Viewing 0.2 cm$^{-1}$ Spectral Transmittances. The inventive auxiliary species option was exercised with a 1 km thick surface layer of HCl. The left-hand side contains the continuous spectrum from 3.2 to 3.7 μm with 10.0 ppm HCl; the right-hand side illustrates the change in absorption arising from varying HCl concentrations for two of the vibrational rotational bands. The doublet structure arises because of the Cl$^{35}$ and Cl$^{37}$ isotopes.

To illustrate the auxiliary species option, IMPROVEMENTS TO MODTRAN4™ Top-Of-Atmosphere (TOA) nadir view calculations were run with a 1 km thick surface layer of HCl embedded into the Mid-Latitude Summer (MLS) model atmosphere. The auxiliary species 0.1 $cm^{-1}$ band model data files, p1_HCl.cBM and p1_HCl.tBM, were read in. Calculations could have been performed with the default HCl profile, but the current objective was to predict the change in spectral signatures with increasing HCl column density. HCl densities of 0.1, 1.0 and 10.0 ppm were input. The transmittance spectra for the HCl component are illustrated in FIG. 3. On the left, the envelope of R and P branch transitions from the (0-1) vibrational transition are displayed. At 0.2 $cm^{-1}$ spectral resolution, the splitting of the $HCl^{35}$ and $HCl^{37}$ isotopes is resolved. This is illustrated for R2 and P3 transitions on the right in FIG. 3.

Figure 4:
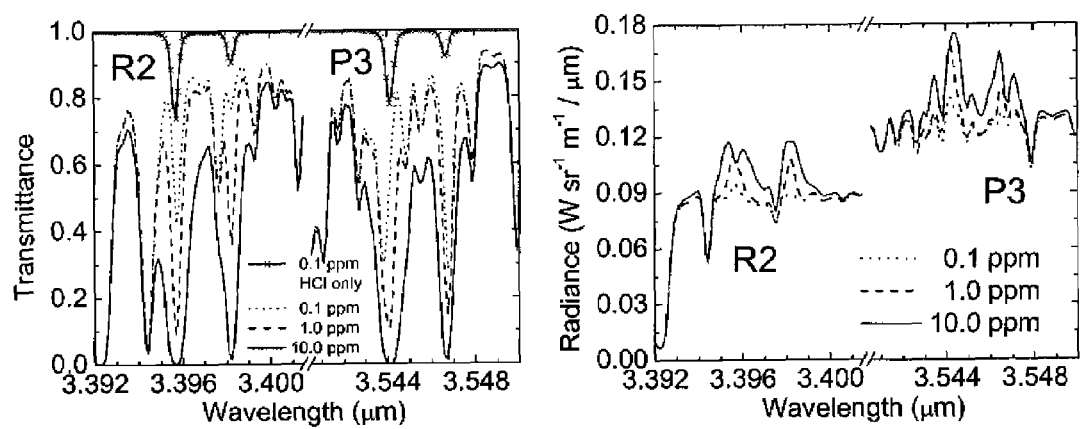
FIG. 4 is two plots also illustrating the auxiliary species aspect of the invention. These are Spectral Transmittances and Thermal Emission as Predicted by an embodiment of the invention for Nadir-Viewing through a MLS atmosphere with a 1 km High HCl layer at the Surface. On the right ths blackbody ground temperature is 10K below the surface air temperature.

The transmittance spectra for the HCl fundamental R2 and P3 vibrational/rotational lines with the HCl surface layer embedded in the MLS atmosphere are shown in FIG. 4 (left). Not surprisingly, the spectra are considerably more complex than the isolated spectra because of overlap with other molecular species, most notably $CH_4$ and $H_2O$.

The thermal emission spectra are also plotted in FIG. 5 (right). In this simulation, the grey-body (emissivity=0.95) surface is modeled with a temperature 10K below the surface air temperature. As a result, the increase in thermal emission resulting from higher HCl concentrations more than compensates for the lowering of surface emission due to the HCl attenuation. If the HCl layer temperature were coincident with the ground surface temperature, the thermal emission spectra would vary minimally with changes to the HCl column density.

Spectrally Varying Aerosol Profiles

MODTRAN™ has always included an option to define up to 4 aerosol types, each specified in a distinct altitude region. Nominally, a boundary layer aerosol density profile is defined for altitude levels up to 2 km, a tropospheric aerosol density profile is defined for altitude levels from 3 to 10 km, a stratospheric aerosol density profile is defined for altitude levels from 11 to 30 km, and a high altitude aerosol density profile is defined above the stratopause. Aerosol spectral optical properties within each of these regions do not vary with altitude; the aerosol concentration profile provide the only variation with altitude. A new Spectral Aerosol Profiles (SAP) option has been developed for the IMPROVEMENTS TO MODTRAN4™ invention. The SAP option allows aerosol spectral extinction coefficients, spectral scattering coefficients, and spectral scattering phase functions all to be entered as a functions of altitude. This enables the IMPROVEMENTS TO MODTRAN4™ invention to more realistically capture the true effect of aerosols on atmospheric radiation transport. As part of this development, the Legendre expansion representation of the SAP aerosol phase function is directly coupled into the DISORT multiple scattering (below). In all the other MODTRAN™ aerosol options, default or user-specified, the scattering phase function is always approximated by a Henyey-Greenstein parameterization for use in multiple scattering computations. This is a critical upgrade for accurate inclusion of aerosols in the scattered radiance calculations.

Whenever the SAP option is exercised within IMPROVEMENTS TO MODTRAN4™, spectral aerosol profile data is read in from an external file, a sample of which is included in Table 2(This example is kindly been provided by Drs. Denis Dion and Vincent Ross, Defence Research and Development Canada, Valcartier, 2005). The first line of the SAP file contains 3 integers: the number of spectral grid points, the number of scattering phase function Legendre moments, and the number of scattering phase function angular points. The second line contains the scattering phase function angular grid in degrees. The next group of lines contains the aerosol data for the first MODTRAN altitude level. There is a separate line for each wavelength. The individual lines contain the altitude level, the spectral wavelength, extinction and scattering coefficients, and phase function data. Legendre moments are listed first followed by phase function values at each of the angular grid points. Subsequent groups of lines contain the data for additional altitude levels.

rithm and summing the boundary term if termination occurs at the hard Earth. This is the essence of Eq. (1). However, since the multiple scattering component of the source function [Eq. (4)] and the downward flux component [Eq. (14)] of the boundary term both depend on LOS spectral radiant intensities themselves, there is an internal coupling that complicates the path integration procedure. MODTRAN™ resolves the self-consistency problem by using a plane-parallel multiple scattering algorithm to compute the LOS spectral radiant intensity dependent contributions. Underlying this procedure is the assumption that multiple scattering in the terrestrial atmosphere is predominately a lower atmosphere effect and therefore well characterized with the locally flat Earth approximation. This ansatz is least accurate for low sun conditions. Thus, for solar elevation angles below ~10°, MODTRAN™ solar radiances carry a relatively high uncertainty.

The MODTRAN™ model includes two multiple scattering algorithms. An analytic two-stream algorithm dubbed the Isaacs approach approximates the multiple scattering source terms with minimal computations. These two-stream results

TABLE 2

Sample Spectral Aerosol Profiles (SAP) Input Data File.

40 64 181

| | | | | | | | | Phase Function vs Angle (°) | | | |
|---|---|---|---|---|---|---|---|---|---|---|---|
| altitude (m) | wavlen | Bext(1/km) | Bsca(1/km) | Pmom1 | Pmom2 | ... | Pmom64 | 0.0000 | 1.0000 | ... | 180.0000 |
| .0003653 | .2000 | .9173681 | .9158943 | 1.0000 | .7966921 | ... | .1319957 | 208.9782 | 193.6871 | ... | .7423355 |
| .0003653 | .3000 | .8726480 | .8726359 | 1.0000 | .8118536 | ... | .1070675 | 208.8804 | 194.0608 | ... | .3700137 |
| .0003653 | .3371 | .8525812 | .8525700 | 1.0000 | .8112088 | ... | .1012243 | 207.9938 | 193.4231 | ... | .3866308 |
| ... | ... | | | | | | | | | | |
| .0003653 | 25.00 | .2620940 | .0969520 | 1.0000 | .7294320 | ... | .0000000 | 38.06391 | 37.61441 | ... | .1531952 |
| .0003653 | 30.00 | .2369326 | .0895308 | 1.0000 | .7221835 | ... | .0000000 | 29.82364 | 29.57460 | ... | .1475345 |
| .0003653 | 40.00 | .2156776 | .0699561 | 1.0000 | .6948593 | ... | .0000000 | 21.41463 | 21.30646 | ... | .1690632 |
| .1260741 | .2000 | .3358318 | .3343440 | 1.0000 | .7796006 | ... | .0807715 | 172.1363 | 160.5204 | ... | .6840323 |
| .1260741 | .3000 | .3008995 | .3008881 | 1.0000 | .7767678 | ... | .0675285 | 161.2990 | 150.9579 | ... | .6125076 |
| .1260741 | .3371 | .2897007 | .2896896 | 1.0000 | .7733779 | ... | .0646587 | 157.8538 | 147.8797 | ... | .6019086 |
| ... | ... | | | | | | | | | | |
| .1260741 | 25.00 | .0616450 | .0247540 | 1.0000 | .6856267 | ... | .0000000 | 17.56935 | 17.49937 | ... | .1463460 |
| .1260741 | 30.00 | .0562292 | .0217360 | 1.0000 | .6611843 | ... | .0000000 | 14.18904 | 14.14785 | ... | .1608776 |
| .1260741 | 40.00 | .0584414 | .0161276 | 1.0000 | .5706048 | ... | .0000000 | 10.02048 | 10.00178 | ... | .2772588 |
| 1993.880 | .2000 | .2613175 | .2602409 | 1.0000 | .7697431 | ... | .0518847 | 152.5157 | 142.7655 | ... | .6152996 |
| 1993.880 | .3000 | .2297381 | .2297099 | 1.0000 | .7593464 | ... | .0413473 | 136.5168 | 128.3560 | ... | .5908967 |
| 1993.880 | .3371 | .2196234 | .2196121 | 1.0000 | .7543240 | ... | .0390868 | 131.9052 | 124.1712 | ... | .5874675 |
| ... | ... | | | | | | | | | | |
| 1993.880 | 25.00 | .0295673 | .0118886 | 1.0000 | .6489874 | ... | .0000000 | 13.93146 | 13.88930 | ... | .1702973 |
| 1993.880 | 30.00 | .0271156 | .0099214 | 1.0000 | .6250932 | ... | .0000000 | 11.57627 | 11.55026 | ... | .1904991 |
| 1993.880 | 40.00 | .0317162 | .0074431 | 1.0000 | .5096798 | ... | .0000000 | 8.037910 | 8.026117 | ... | .3562035 |

In the RTE, the absorption and scattering coefficients, Eq. (3), and the effective phase function, Eq. (5), are all express as sums of individual species contribution. When the SAP options is exercised in IMPROVEMENTS TO MODTRAN4™, the SAP aerosol is treated as one of these species. The extinction coefficient, scattering coefficient, and required phase function profile data are spectrally interpolated (linearly in wavelength) at the central bin frequency within the band model spectral loop. The extinction and scattering coefficients are modeled as varying exponentially with altitude, while the scattering phase functions and the Legendre coefficient are linearly interpolated in altitude. The result is a first principles treatment of the aerosol contributions.

Multiple Scattering via the DISORT Algorithm

MODTRAN™ computes LOS spectral radiant intensities by integrating the attenuated spectral source function along the path defined by its spherical refractive geometry algoare best suited for calculation of spatially integrated radiances (fluxes) and thermal scatter contributions. However, the accuracy of the 2-stream solar scatter radiant intensities is relatively poor, typically ±20%, but factor of 2 errors are not uncommon in the shortwave end of visible spectral region (blue). For higher fidelity results, MODTRAN™ employs the DISORT discrete ordinate algorithm to compute multiple scatter radiances. In this section, the DISORT algorithm and its IMPROVEMENTS TO MODTRAN4™ interface are described.

Chandrasekhar's Solution to the Plane-Parallel Atmosphere RTE

DISORT explicitly solves the integral-differential RTE for a horizontally-homogeneous plane-parallel atmosphere with no diffuse radiation impingent on the top of atmosphere (TOA) and with an emitting and reflecting ground surface:

$$\mu \frac{dI(\Omega; \tau^\downarrow)}{d\tau^\downarrow} = I(\Omega; \tau^\downarrow) - J(\Omega; \tau^\downarrow) \tag{46}$$

Source Function $$J(\Omega; \tau^\downarrow) \equiv (1 - \omega_{\tau^\downarrow})B(T_{\tau^\downarrow}) +$$

$$\omega_{\tau^\downarrow}\left[p(\Omega, \Omega^{sun}; \tau^\downarrow)e^{\tau^\downarrow/\mu^{sun}}F^{sun} + \int_{4\pi} p(\Omega, \Omega'; \tau^\downarrow)I(\Omega'; \tau^\downarrow)d\Omega'\right]$$

$$\omega_{\tau^\downarrow} \equiv b^{sct}(\tau^\downarrow)/b(\tau^\downarrow)$$

Boundary Conditions $$I(+\mu, \phi; \tau_g^\downarrow) =$$

$$\varepsilon(+\mu, \phi)B(T_g) + \mu^{sun}f(+\mu, \phi, \mu^{sun}, \phi^{sun})e^{-\tau_g^\downarrow/\mu^{sun}}F^{sun};$$

$$I(-\mu, \phi; 0) = 0 + \int_0^1 \int_0^{2\pi} I(-\mu', \phi'; \tau_g^\downarrow)f(+\mu, \phi, -\mu', \phi')\mu'd\phi'd\mu'.$$

The top equation in this set is the path optical depth derivative of the integral RTE, Eq. (1), for a plane-parallel atmosphere. Since refraction and spherical Earth effects are excluded, the path solid angle $\Omega[\equiv(\mu,\phi)]$ is constant for a given LOS. The reference to position has also been dropped as an argument of the BRDF because the Earth surface is modeled as horizontally homogeneous. For notational simplicity, the spectral frequency subscript has also been dropped from Eq. (46) and all subsequent equations in this section, even though all quantities other than the temperatures and angles are spectrally dependent. Finally, the path optical depth is represented as the quotient of the path nadir optical depth measured from the TOA $\tau^\downarrow$ and the cosine of the path zenith angle with the ground value, $\tau_g^\downarrow$, equal to the total atmosphere nadir extinction optical depth. Any remaining references to position s have been replaced by references to the nadir optical depth $\tau^\downarrow$ because of the lack of horizontal variability.

In order to facilitate solving the plane parallel atmosphere radiation transport problem, two additional model assumptions are made up front: (1) the scattering phase function is modeled as a function of the angle $\Theta$ between the incident and outgoing beams, $p(\Omega,\Omega';\tau^\downarrow)=p(\Theta;\tau^\downarrow)$; and (2) the surface BRDF is modeled as a function of the incoming and outgoing zenith angles and of the relative azimuth angle, but not of the incoming and outgoing azimuth angles independently, i.e., $f(\Omega,\Omega')=f(\mu,-\mu',\phi-\phi')$. These assumptions limit DISORT's ability to precisely model physical phenomena such as preferential orientation of ice particles in cirrus clouds and plowed fields on the Earth's surface. However, under most terrestrial atmospheric scenarios, it is quite reasonable to model suspended particles as randomly oriented and the Earth surface as locally isotropic.

DISORT follows a 4-step approach, originally laid out by Chandrasekhar, to solve the integral-differential RTE. In developing the DISORT model, Stamnes and his coworkers solved the previous unsolved and challenging problem of creating a numerically stable realization of the Chandrasekhar approach.

Step 1: Factoring the Azimuth Dependence

The azimuth dependence of the RTE is factored from the integral-differential RTE by expanding the radiance and bidirectional reflectivity in Fourier cosine series, and expanding the scattering phase function in Legendre polynomials, $P_l(\mu)$, and unit normalized associated Legendre polynomials, $\Lambda_l^m(\mu)$:

$$I(\Omega; \tau^\downarrow) = \sum_{m=0}^{2M-1} I^m(\mu; \tau^\downarrow)\cos m(\phi^{sun} - \phi); \tag{47}$$

$$f(\mu, -\mu', \phi - \phi') = \sum_{m=0}^{2M-1} f^m(\mu, -\mu')\cos m(\phi - \phi');$$

and $$p(\Theta; \tau^\downarrow) = \sum_{\ell=0}^{2M-1} (2\ell + 1)\frac{g_{\tau^\downarrow}^\ell}{4\pi}P_\ell(\cos\Theta)$$

$$= \sum_{\ell=0}^{2M-1} (2\ell + 1)\frac{g_{\tau^\downarrow}^\ell}{4\pi}$$

$$\left\{P_\ell(\mu)P_\ell(\mu') + 2\sum_{m=1}^{\ell} \Lambda_\ell^m(\mu)\Lambda_\ell^m(\mu')\cos(\phi - \phi')\right\}.$$

In these equations, the $I^m(\mu;\tau^\downarrow)$ are the azimuth moment radiant intensities, the $f^m(\mu;-\mu')$ are the azimuth moment BRDFs, the $g_{\tau^\downarrow}^l$ are the scattering phase function Legendre moments, and 2M is the number of Legendre moments (l=0 to 2M-1). These expansions yield independent/orthogonal integral differential equations for each m component:

$$\mu\frac{dI^m(\mu; \tau^\downarrow)}{d\tau^\downarrow} = I^m(\mu; \tau^\downarrow) - J^m(\mu; \tau^\downarrow)(m = 0, 1, \ldots, 2M-1) \tag{48}$$

Source Function $$J^m(\mu; \tau^\downarrow) =$$

$$\omega_{\tau^\downarrow}\left\{(2 - \delta_{m0})F^{sun}\left[\sum_{\ell=m}^{2M-1'} (-1)^{\ell+m}(2\ell + 1)\frac{g_{\tau^\downarrow}^\ell}{4\pi}\Lambda_\ell^m(\mu)\Lambda_\ell^m(\mu^{sun})\right] + \int_{-1}^1 I^m(\mu'; \tau^\downarrow)\left[\sum_{\ell=m}^{2M-1'} (2\ell + 1)\frac{g_{\tau^\downarrow}^\ell}{2}\Lambda_\ell^m(\mu)\Lambda_\ell^m(\mu')\right]d\mu'\right\} +$$

$$\delta_{m0}(1 - \omega_{\tau^\downarrow})B(T_{\tau^\downarrow})$$

Boundary Conditions $$I^m(+\mu; \tau_g^\downarrow) = \delta_{m0}\varepsilon(\mu)B(T_g) + \mu^{sun}f^m(\mu, -\mu^{sun})e^{-\tau_g^\downarrow/\mu^{sun}}F^{sun};$$

$$I^m(-\mu; 0) = 0 + (1 + \delta_{m0})\int_0^1 I^m(-\mu'; \tau_g^\downarrow)f^m(+\mu, -\mu')\mu'd\mu'$$

Note that in the absence of solar radiation, only the m=0 problem needs to be solved. This is also true if there is azimuthal symmetry resulting from either a zenith sun or a vertical/nadir LOS.

Step 2: Introducing Discrete Ordinates

In the second step of the Chandrasekhar procedure, the independent integral-differential equations are each converted into a system of 2N coupled ordinary differential equations (ODE's) by applying the discrete ordinate approximation to the cosine zenith integrals.

$$\mu_i \frac{dI^m(\mu_i;\tau^\downarrow)}{d\tau^\downarrow} = I^m(\mu_i;\tau^\downarrow) - J^m(\mu_i;\tau^\downarrow)(i=\pm1,\pm2,\ldots,\pm N); \quad (49)$$

Source Function $$J^m(\mu;\tau^\downarrow) =$$

$$\omega_{\tau^\downarrow}\left\{(2-\delta_{m0})F^{sun}\left[\sum_{\ell=m}^{2M-1'}(-1)^{\ell+m}(2\ell+1)\frac{g_{\tau^\downarrow}^\ell}{4\pi}\Lambda_\ell^m(\mu)\Lambda_\ell^m(\mu_i^{sun})\right]+\right.$$

$$\left.\sum_{\substack{j=-N\\j\neq 0}}^N w_j I^m(\mu_j;\tau^\downarrow)\left[\sum_{\ell=m}^{2M-1'}(2\ell+1)\frac{g_{\tau^\downarrow}^\ell}{2}\Lambda_\ell^m(\mu)\Lambda_\ell^m(\mu_j)\right]\right\}+$$

$$\delta_{m0}(1-\omega_{\tau^\downarrow})B(T_{\tau^\downarrow});$$

Boundary Conditions $$I^m(+\mu_i;\tau_g^\downarrow) = \delta_{m0}\varepsilon(\mu_i)B(T_g) + \mu^{sun}f^m(\mu_i,-\mu^{sun})e^{-\tau_g^\downarrow/\mu^{sun}}F^{sun};$$

$$I^m(-\mu_i;0) = 0 + (1+\delta_{m0})\sum_{j=1}^N w_j\mu_j I^m(-\mu_j;\tau_g^\downarrow)f^m(+\mu,-\mu_j)$$

$$(i = +1,+2,\ldots,+N)$$

DISORT employs a double Gaussian quadrature, with paired cosine angles, $\mu_j = -\mu_{-j}$, symmetric in each hemisphere about $\mu = \frac{1}{2}$ and having a common Gaussian weight, $w_j = w_{-j}$.

Step 3: Simplifying Optical Depth Dependence via Atmospheric Layering

In the third step of the Chandrasekhar procedure, the optical depth dependence of the atmospheric single scattering albedo, the scattering phase function and the Planck emission is parameterized so that an analytic matrix solution to the system of ODE's can be derived. This is accomplished by partitioning the atmosphere into l=1 to L layers with l=0 to L level boundaries. Altitudes $z_0$=TOA to $z_L$=ground, nadir optical depths $\tau_0^\downarrow$=0 to $\tau_L^\downarrow=\tau_g^\downarrow$, and temperatures $T_0$ to $T_L$ are specified at each altitude level. Scattering properties are modeled as constants within each layer:

$$\omega_l \equiv \int_{z_{l-1}}^{z_l} b^{sct}(z)dz \bigg/ \int_{z_{l-1}}^{z_l} b(z)dz; \quad (50)$$

$$g_l^\ell \equiv \int_{z_{l-1}}^{z_l} g_{\tau^\downarrow}^\ell(z)b^{sct}(z)dz \bigg/ \int_{z_{l-1}}^{z_l} b^{sct}(z)dz,$$

while Planck emission is characterized as varying linearly with nadir optical depth through each layer:

$$B_l(T_{\tau^\downarrow}) = B(T_{l-1}) + \frac{\tau^\downarrow - \tau_{l-1}^\downarrow}{\tau_l^\downarrow - \tau_{l-1}^\downarrow}[B(T_l) - B(T_{l-1})]; \quad (51)$$

$$\tau_{l-1}^\downarrow \leq \tau^\downarrow \leq \tau_l^\downarrow.$$

A general solution can be derived for the m-dependent RTE within each atmospheric layer given this parameterization of optical depth dependence:

$$I_l^m(\mu_i;\tau^\downarrow) = \delta_{m0}[Y_{0l}(\mu_i) + Y_{1l}(\mu_i)\tau^\downarrow] + \quad (52)$$

$$Z_l^m(\mu_i)e^{-\tau^\downarrow/\mu^{sun}} + \sum_{\substack{j=-N\\j\neq 0}}^N C_{jl}^m G_{jl}^m(\mu_i)e^{-k_{jl}^m\tau^\downarrow};$$

$$\tau_{l-1}^\downarrow \leq \tau^\downarrow \leq \tau_l^\downarrow.$$

In Eq. (52), the $Y_{0l}(\mu_i)$ and $Y_{1l}(\mu_i)$ arise as a particular solution to the thermal source problem and are obtained by solving a system 4N linear equations. Similarly, the $Z_l^m(\mu_i)$ are a particular solution to the solar source problem, obtained by solving a system of 2N linear equations for each value of m. The $k_{jl}^m$ and $G_{jl}^m$ are the eigenvalues and eigenvectors, respectively, that arise in solving the hormogeneous plane-parallel RTE problem [$F^{sun}$=0; $B_j$=0], and the $C_{jl}^m$ are the constants of integration that must be determined from boundary and layer continuity conditions.

Step 4: Applying Boundary and Continuity Equations

For each of the azimuth moments m, the L atmospheric layers each contain 2N constants of integration. These values are determined from the (2N)×L linear boundary and continuity equations:

$$I_1^m(-\mu_i;\tau_0^\downarrow = 0) = 0 \quad (53)$$

$$(i = +1,+2,\ldots,+N);$$

$$I_{l-1}^m(-\mu_i;\tau_{l-1}^\downarrow) = I_l^m(-\mu_i;\tau_{l-1}^\downarrow)$$

$$(l = 2,3,\ldots,L; i = \pm1,\pm2,\ldots,\pm N);$$

$$I_L^m(+\mu_i;\tau_g^\downarrow) = \delta_{m0}\varepsilon(\mu_i)B(T_g) + \mu^{sun}f^m(\mu_i,-\mu^{sun})e^{-\tau_g^\downarrow/\mu^{sun}}F^{sun} +$$

$$(1+\delta_{m0})\sum_{j=1}^N w_j\mu_j I^m(-\mu_j;\tau_g^\downarrow)f^m(+\mu_i,-\mu_j)(i=+1,+2,\ldots,+N).$$

Solving for these constants is the most computationally time intensive step in DISORT.

Once the constants of integration have been calculated, the specific requested spectral radiant intensities and horizontal fluxes can be computed. The interpolated spectral radiant intensity in direction ($\pm\mu,\phi$) and at an arbitrary nadir optical depth $\tau^\downarrow$ within the plane-parallel atmosphere is computed by inserting the integral RTE into the radiant intensity expression of Eq. (47):

$$I(+\mu,\phi;\tau^\downarrow) = \quad (54)$$

$$\sum_{m=0}^{2M-1}\left\{I^m(+\mu;\tau_L^\downarrow)e^{-\frac{\tau^\downarrow-\tau_L^\downarrow}{\mu}} + \int_{\tau^\downarrow}^{\tau_L^\downarrow}J^m(+\mu;\tau^{\downarrow'})e^{-\frac{\tau^{\downarrow'}-\tau^\downarrow}{\mu}}\frac{d\tau^{\downarrow'}}{\mu}\right\}$$

$$\cos m(\phi^{sun}-\phi);$$

$$I(-\mu,\phi;\tau^\downarrow) = \sum_{m=0}^{2M-1}\left\{\int_0^{\tau^\downarrow}J^m(-\mu;\tau^{\downarrow'})e^{-\frac{\tau^\downarrow-\tau^{\downarrow'}}{\mu}}\frac{d\tau^{\downarrow'}}{\mu}\right\}\cos m(\phi^{sun}-\phi).$$

The azimuth moments of the source function $J^m(\pm\mu;\tau^\downarrow)$ are defined by Eq. (49). Substitution of Eqs. (50), (51) and (52) for the nadir optical depth dependent terms yields simple exponential integrals that are evaluated analytically. For the upward and downward flux calculations, only m=0 terms contribute. The fluxes are computed from the Gaussian quadrature integral representation:

$$F^+(\tau^\downarrow) \cong 2\pi \sum_{i=1}^{N} w_i \mu_i I^0(+\mu; \tau^\downarrow); \quad (55)$$

$$F^-(\tau^\downarrow) \cong \mu^{sun} F^{sun} e^{-\tau^\downarrow/\mu^{sun}} + 2\pi \sum_{i=1}^{N} w_i \mu_i I^0(-\mu; \tau^\downarrow);$$

$$F^-(\tau_g^\downarrow) \cong \mu^{sun} F^{sun} e^{-\tau_g^\downarrow/\mu^{sun}} + F_v^\downarrow(s_g).$$

In the last line of Eq. (55), the relationship between the total (direct+diffuse) downward flux at the ground and the diffuse downward flux of Eq. (14) is explicitly presented.

The MODTRAN™ Interface to DISORT

In principle, MODTRAN™ could be used solely as the optical property and geometry specifier for DISORT, defining the DISORT inputs as a function of wavelength, and DISORT used as the RT engine, the generator of the RT outputs. However, in this mode, the MODTRAN™ ability to incorporate spherical refractive effects would be lost. As described above, DISORT is instead only used to compute the multiple scattering and surface downward flux contributions to Eq. (13). In this sub-section, the precise interface is laid out. The subsection begins with a description of DISORT convergence issues, the delta-M method and its impact on the MODT-RAN™ interface. The IMPROVEMENTS TO MODT-RAN4™ method of defining DISORT inputs is described next, and that is followed by a description of special uses of DISORT via the IMPROVEMENTS TO MODTRAN4™.

DISORT Convergence, the Delta-M Method and Radiant Intensities

Atmospheric aerosol and cloud particulates typically possess highly forward peaked scattering phase functions. Accurate representation of these functions using a Legendre expansion, Eq. (47), requires hundreds of terms. Computation times grow rapidly with the number of discrete ordinate streams, which DISORT couples to the number of azimuth terms.

To alleviate the convergence problem, the delta-M method was introduced. In this method, the scattering phase function is represented as a sum of a forward peaked Dirac-delta function δ(1-cos Θ) and a Legendre expansion:

$$p'(\Theta; \tau^\downarrow) = \frac{1}{4\pi}\left[2f\delta(1-\cos\Theta) + (1-f)\sum_{\ell=0}^{2M-1}(2\ell+1)g_{\tau^\downarrow}^{\prime\ell} P_\ell(\cos\Theta)\right]; \quad (56)$$

$$g_{\tau^\downarrow}^{\prime\ell} = \frac{g_{\tau^\downarrow}^\ell - f}{1-f} (\ell = 0, \ldots, 2M-1);$$

$$f = g_{\tau^\downarrow}^{2M}.$$

Here, the delta-M method expansion coefficients $g'_{\tau^\downarrow}{}^\ell$ are defined by requiring preservation of the overall Legendre expansion up to order 2M−1, and, as indicated here, the extra parameter f is set by fitting one additional term from the expansion. The delta-M method changes the assumption used for the higher order Legendre coefficients; instead of setting these coefficients to zero, Eq. (47), they are set to $g'_{\tau^\downarrow}{}^{2M}$. The Legendre expansion coefficients from observed particulate phase functions typically fall off quite slowly, so the constant value that results from the delta-M method is a more realistic representation. From an alternative perspective, the integrals used to compute the traditional scattering phase function Legendre expansion coefficients are dominated by the forward peak, which yields a poor representation for off-peak angles. By factoring out the forward peak, Eq. (56) allows the phase function in the ε<Θ<180° angular region (ε small) to be much better characterized by the expansion.

With the delta-M method, accurate spectral radiant intensities and fluxes can generally be computed with as few as 4, 8 or 16 streams. Substituting of the delta-M expansion for the phase function into the RTE transforms it into an identical equation, but with p, τ↓, and ω replaced by p', τ'↓, and ω', where the later two quantities are defined by:

$$d\tau'^\downarrow = (1 - \omega_l f)d\tau^\downarrow; \quad (57)$$

$$\omega'_l = \frac{1-f}{1-\omega_l f}\omega_l.$$

DISORT automatically implements these transformations.

The one obvious drawback of the delta-M method is that the transformed radiant intensities are somewhat inaccurate for very near forward scattering scenarios, such as occurs in the study of the solar aureole, because the finite width of the forward peak is not characterized. To improve near forward scattering accuracy, DISORT provides an option to invoke a series of radiant intensity corrections developed by Nakajima and Tanaka. In these corrections, the plane-parallel atmosphere single scatter solar radiant intensity is explicitly subtracted from the diffuse solar radiant intensity and then added back in using a high order Legendre expansion for the scattering phase function. Additional, less dramatic Nakajima and Tanaka corrections improve higher order solar scattering intensity terms.

For DISORT runs from within MODTRAN™, it is important that the Nakajima and Tanaka corrections not be invoked. MODTRAN™ itself subtracts the plane-parallel single scatter solar contribution from the DISORT at-source solar radiant intensity for each layer l, $\Delta I_l(\mu,\phi)$:

Downward Viewing (58)

$$\Delta I_l^{mss}(+\mu,\phi) =$$

$$\Delta I_l^{sun}(+\mu,\phi) - \left(\frac{\mu^{sun}}{\mu+\mu^{sun}}\right)F^{sun}\omega_l p'_l(\Theta)\left[t_{l-1\to sun} - e^{-\Delta\tau_l^\downarrow/\mu}t_{l\to sun}\right];$$

$$\Delta I_l(+\mu,\phi) \equiv I(+\mu,\phi;\tau_{l-1}^\downarrow) - e^{-\Delta\tau_l^\downarrow/\mu}I(+\mu,\phi;\tau_l^\downarrow);$$

Upward Viewing $$\Delta I_l^{mss}(-\mu,\phi) =$$

$$\Delta I_l^{sun}(-\mu,\phi) - \left(\frac{\mu^{sun}}{\mu-\mu^{sun}}\right)F^{sun}\omega_l p'_l(\Theta)\left[t_{l\to sun} - e^{-\Delta\tau_l^\downarrow/\mu}t_{l-1\to sun}\right];$$

$$\Delta I_l(-\mu,\phi) \equiv I(-\mu,\phi;\tau_l^\downarrow) - e^{-\Delta\tau_l^\downarrow/\mu}I(-\mu,\phi;\tau_{l-1}^\downarrow).$$

In this equation, $\Delta I_l^{mss}(\pm\mu,\phi)$ is the at-source multiple (no single) scatter solar radiant intensity from layer l; $\omega_l$ and $p'_l(\Theta)$ are the single scattering albedo and delta-M scattering phase function within layer l; $\Delta\tau_l^\downarrow$ is the nadir optical depth through layer l; $t_{l\to sun}$ is the solar path transmittance from the bottom of layer l; and $t_{l-1\to sun}$ is the solar path transmittance from the top of layer l. MODTRAN™ subsequently adds in the spherical refractive geometry single scatter solar radiant intensity. MODTRAN™ computes the species scattering phase functions either from an analytic form (for Rayleigh and Henyey-Greenstein representations) or from a scattering angle dependent table. For user-defined scattering phase functions, both the Legendre coefficients and the tabulated values are required inputs to insure that the Legendre expansion does not have to be relied upon for the single scatter calculation.

MODTRAN incorporates the DISORT multiple scattering layer contributions into its LOS radiant intensity by first defining a DISORT thermal and multiple scattering solar layer source terms, $\Delta J_l^{thm}$ and $\Delta J_l^{mss}$:

$$\Delta J_l^{thm} \equiv \frac{\Delta I_l^{thm}(\pm\mu,\phi)}{1-e^{-\Delta\tau_l^\downarrow/\mu}};$$

$$\Delta J_l^{mss} \equiv \frac{\Delta I_l^{mss}(\pm\mu,\phi)}{1-e^{-\Delta\tau_l^\downarrow/\mu}}.$$

(59)

These source terms are then multiplied by refractive path transmittance differences and added to the single scatter solar contributions:

$$\langle I_0(\Omega)\rangle = \langle t_{0\to s}I_s(\Omega)\rangle - $$

$$\int_0^s \langle t_{0\to s'\to sun}^{mol\_abs}\rangle \overline{t_{0\to s'\to sun}^{part\_abs}}\,\overline{t_{s'\to sun}^{sct}}\,\overline{F^{sun}}\,\overline{p_{s'}}(\Omega,\Omega^{sun})\left(\frac{d\overline{t_{0\to s'}^{sct}}}{ds'}\right)ds' + $$

$$\sum_{\sigma\,segments}\left\{\langle t_{0\to s_{\sigma-1}}^{mol\_abs}\rangle\overline{t_{0\to s_{\sigma-1}}^{part\_abs}}\,\overline{t_{0\to s_{\sigma-1}}^{sct}} - \langle t_{0\to s_\sigma}^{mol\_abs}\rangle\overline{t_{0\to s_\sigma}^{part\_abs}}\,\overline{t_{0\to s_\sigma}^{sct}}\right\}$$

$$(\Delta J_{l\sigma}^{thm} + \Delta J_{l\sigma}^{mss})$$

(60)

This procedure enables the band model molecular transmittance COG to be incorporated into the multiple scatter calculation.

DISORT I/O for MODTRAN™

The complete list of inputs to the plane-parallel multiple scattering algorithms in MODTRAN™ is quite modest. As noted above, the atmosphere is stratified with each layer l characterized by a nadir optical depth, $\Delta\tau_l^\downarrow$, and layer averaged values for the single scattering albedo, $\omega_l$, and the scattering phase function Legendre moments, $g_l^l$. In addition, layer boundaries are characterized by altitude level temperatures, $T_l$. Other than this profile data, the only inputs are spectral range (required for the Planck function evaluation), TOA solar irradiance, solar angle and observer zenith and relative solar azimuth angles.

In principle, solving for layer source functions, $\Delta J_l$, is simplest in the optical thin limit. However, this limit is occasionally problematic for DISORT. To simplify the source code, the developers of DISORT made a conscience effort to avoid branching for special cases. As a result, inclusion of layers with a very small nadir optical depth, $\Delta\tau_l^\downarrow$, can produce numerical instabilities. This problem is avoided by merging MODTRAN™ layers to insure that $\Delta\tau_l^\downarrow$ exceeds a 0.0001 threshold. This actually provides the added benefit of speeding up the DISORT calculations, because computation time is proportional to the number of computation layers. The DISORT output of vertical flux profiles are redefined onto the finer gridded MODTRAN™ levels via optical depth weighted interpolations. The coarse layer source function values are assigned without modification to the MODT-RAN™ sub-layers with one caveat: the thermal source for thin layers (nadir optical depth of less than 0.001) is set to the layer blackbody emission value (the conservative scattering approximation).

The calculation of the layer source functions is numerically more stable if the solar and thermal DISORT scatter calculations are performed independently, especially for azimuth dependent scenarios. One reason for this is that when DISORT solar scatter calculations are performed and the nadir absorption optical depth is large, DISORT only calculates the solar scattering contributions for the upper atmosphere; atmospheric layers for which the nadir absorption optical depth exceeds 10 are excluded. However, the dark layers are not excluded from the solar calculations if thermal scatter contributions are computed simultaneously. Combining of solar and thermal calculations results in numerical instabilities. Thus, whenever MODTRAN performs azimuth dependent scattering DISORT calculations, the solar and thermal contributions are computed from separate calls to DISORT.

Additionally, special cases can arise that are problematic for DISORT and either require special handling by the MODTRAN™ interface or complete avoidance. Three of these cases involve a solar geometry. If the solar zenith angle is too close to one of the Gaussian double quadrature angles, the IMPROVEMENTS TO MODTRAN4™ package dithers the solar angle to insure that $|\mu_i-\mu_{sun}|>\mu_{sun}/10{,}000$. If the view zenith angle is near coincident with the solar zenith angle, the view angle is perturbed as follows:

$$\text{If } |\mu_{sun}+\mu_o|<0.002 \Rightarrow \mu_o' = \begin{cases} -(\mu_{sun}+0.002) & \text{for } \mu_{sun}\le 0.5 \\ -(\mu_{sun}-0.002) & \text{for } \mu_{sun}>0.5 \end{cases},$$

(61)

where $\mu_o$ is the original view cosine zenith and $\mu_o'$ is the view cosine zenith used in the DISORT algorithm. Finally, if the sun is below the horizon ($\mu_{sun}\le 0$), then solar multiple scattering contributions are set to zero. Spectrally, if the single scattering albedo is too close to unity for any layer, it is lowered to a value that will insure a numerically stable solution; this can lead to inaccurate scattered radiances for a purely Rayleigh atmosphere.

MODTRAN™ Atmospheric Correction Data File

The observed solar scatter radiance at nadir optical depth $\tau^\downarrow$ measured from an Earth viewing Visible/Near-Infrared (VNIR) through Shortwave-Infrared (SWIR) hyperspectral imager along the $\Omega_0$ direction can be conveniently partitioned into three components: the scattered only by atmosphere radiance $I^{atm}(\Omega_0;\tau^\downarrow)$ the directly transmitted from ground reflected radiance $I_{dir}^{gnd}(\Omega_0;\tau^\downarrow)$, and the diffusely transmitted from ground reflected radiance $I_{dif}^{gnd}(\Omega_0;\tau^\downarrow)$:

$$I(\Omega_o;\tau^\downarrow) = I^{atm}(\Omega_o;\tau^\downarrow) + I_{dir}^{gnd}(\Omega_o;\tau^\downarrow) + I_{dir}^{gnd}(\Omega_o;\tau^\downarrow).$$

(62)

As before, the spectral index has been omitted for notational simplicity. This partitioning is particularly useful for remote sensing applications because it provides a distribution of ground information content: $I^{atm}$ contains no information about the ground; $I_{dir}^{gnd}$ is directly proportional to the imaged pixel reflectance; and $I_{dif}^{gnd}$ provides data about surrounding ground pixels.

For a specified atmosphere, the scattered only by atmosphere solar radiance is computed in DISORT by setting the upper illumination at the lower boundary, $I^m(+\mu;\tau_g^\downarrow)$, to zero and dropping the thermal contributions from Eq. (46):

$$I^{atm}(\Omega_o; \tau^\downarrow) = I(\Omega_o; \tau^\downarrow) \qquad (63)$$

Source Function $$J(\Omega; \tau^\downarrow) \equiv$$
$$\omega_{\tau^\downarrow}\left[p(\Omega, \Omega^{sun}; \tau^\downarrow)e^{-\tau^\downarrow/\mu^{sun}}F^{sun} + \int_{4\pi}p(\Omega, \Omega'; \tau^\downarrow)I(\Omega'; \tau^\downarrow)d\Omega'\right]$$

Boundary Conditions $$I(+\mu, \phi; \tau_g^\downarrow) = 0;$$
$$I(-\mu, \phi; 0) = 0$$

In practice, the lower boundary condition is specified by setting a thermal flag to false and setting the surface reflectance to zero.

The directly transmitted from ground reflected radiance, $I_{dir}^{gnd}$ can be expressed as a function of ground-dependent only and atmosphere-dependent only terms if the imaged pixel is modeled as a Lambertian reflector with BRDF, $f(+\mu,-\mu')$, equal to $\alpha/\pi$:

$$I_{dir}^{gnd}(\Omega_o; \tau^\downarrow) = \frac{\mu^{sun}F^{sun}t_{total}^{sun\rightarrow gnd}}{1-\langle\alpha\rangle\sigma^{gnd}}\left(\frac{\alpha}{\pi}\right)t_{direct}^{obs\rightarrow gnd}. \qquad (64)$$

In this expression, the product $\mu^{sun}F^{sun}$ equals the top-of-atmosphere (TOA) solar downward horizontal flux. Multiplying this product by the sun-to-ground total (direct+diffuse) transmittance, $t_{total}^{sun\rightarrow gnd}$ ($=t_{direct}^{sun\rightarrow gnd}+t_{diffuse}^{sun\rightarrow gnd}$) results in the expression for the surface downward solar flux given a black (i.e., non-reflecting) and cold (i.e., non-emitting) ground. If the ground is actually a Lambertian reflector with a positive spatially-averaged surface albedo, i.e., $\langle\alpha\rangle>0$, then the product $\langle\alpha\rangle\sigma^{gnd}$ equals the fraction of initial downward illumination at the ground that will return to the bottom of the atmosphere after a single ground reflection, where $\sigma^{gnd}$ is the atmospheric spherical albedo from the ground. The atmospheric spherical albedo is defined as the fraction of lower boundary isotropic illumination that will scatter back to the ground. The multiple reflections expression is a geometric sum:

$$1 + \langle\alpha\rangle\sigma^{gnd} + (\langle\alpha\rangle\sigma^{gnd})^2 + (\langle\alpha\rangle\sigma^{gnd})^3 + \cdots = \frac{1}{1-\langle\alpha\rangle\sigma^{gnd}}. \qquad (65)$$

Thus, the left-most quotient on the right-hand side of Eq. (64) equals the total downward solar flux at the ground. A final multiplication of this surface flux by the Lambertian reflectance and the direct transmittance to the observer, $t_{direct}^{obs\rightarrow gnd}$, provides the expression for the directly transmitted ground reflected radiance.

MODTRAN™ itself computes direct path transmittances, $t_{direct}^{sun\rightarrow gnd}$ and $t_{direct}^{obs\rightarrow gnd}$. The remaining atmosphere-dependent only terms of Eq. (64) are readily determined using DISORT by appealing to the RT reciprocity principle. As noted by Stamnes, the plane albedo from and diffuse transmissivity through a vertically inhomogeneous planetary atmosphere can be expressed in terms of normalized emergent diffuse intensities from isotropic incident illumination:

$$t_{diffuse}^{sun\rightarrow gnd} = \frac{I^0(+\mu^{sun}; 0)}{I^0(+\mu; \tau_g^\downarrow)}; \qquad (66)$$

$$\sigma^{gnd}(-\mu') = \frac{I^0(-\mu'; \tau_g^\downarrow)}{I^0(+\mu; \tau_g^\downarrow)};$$

Source Function $$J^0(\mu; \tau^\downarrow) = \omega_{\tau^\downarrow}\left\{\sum_{\substack{j=-N\\j\neq 0}}^{N}w_jI^0(\mu_j; \tau^\downarrow)\left[\sum_{\ell=0}^{2M-1'}(2\ell+1)\frac{g_{\tau^\downarrow}^\ell}{2}\Lambda_\ell^0(\mu)\Lambda_\ell^0(\mu_j)\right]\right\}$$

Boundary Conditions $$I^0(+\mu; \tau_g^\downarrow) = \text{constant} > 0;$$
$$I^0(-\mu_i; 0) = 0,$$

where the plane albedo, $\sigma^{gnd}(-\mu')$, is related to the spherical albedo, $\sigma^{gnd}$, by the integral equation $$\sigma^{gnd} = \int_{2\pi}\sigma^{gnd}(-\mu')\mu'd\Omega'. \qquad (67)$$

The beauty of these equations is that there is no azimuth dependence, so only the m=0 solution need be computed, and the particular solution does not have to be calculated because the boundary and the external source and the emitted source terms are all zero. Thus, these calculations are computationally modest.

The final term of Eq. (62) is the diffusely transmitted ground reflected radiance:

$$I_{dif}^{gnd}(\Omega_o; \tau^\downarrow) = \frac{\mu_{sun}F^{sun}t_{total}^{sun\rightarrow gnd}}{1-\langle\alpha\rangle\sigma^{gnd}}\left(\frac{\langle\alpha\rangle}{\pi}\right)t_{emb\_dif}^{obs\rightarrow gnd}. \qquad (68)$$

In this equation, the total downward solar flux, the left-most quotient on the right-hand side, is multiplied by the spatially averaged Lambertian reflectance and a medium embedded diffuse transmittance term, $t_{emb\_dif}^{obs\rightarrow gnd}$. In remote sensing literature, this transmittance term is typically simply referred to as the observer-to-ground diffuse transmittance. However, the observer-to-ground diffuse transmittance is defined as the fraction of parallel beam illumination along the observer view direction that would transmit through a bounded medium. From the principle of reciprocity, this equals illumination-normalized radiation exiting the medium in the reverse observer view direction when isotropically illuminated from below. If the sensor is embedded within the medium, or more specifically, the Earth's atmosphere, then Eq. (68) needs to include the back-scattering from atmosphere above the observer, such as that illustrated in the trajectory of FIG. 5. The term medium embedded diffuse transmittance is being introduced to capture all the ground leaving radiance that reaches the observer after being scattered by atmosphere without further interacting with the ground surface. This quantity is calculated as follows:

$$t_{emb\_dif}^{obs\rightarrow gnd} = \frac{I^0(+\mu^{gnd\rightarrow obs}; \tau^\downarrow)}{I^0(+\mu; \tau_g^\downarrow)}; \qquad (69)$$

$$0 \leq \tau^\downarrow \leq \tau_g^\downarrow$$

-continued

Source Function $$J^0(\mu; \tau^\perp) = \omega_{\tau^\perp}\left\{\sum_{\substack{j=-N \\ j\neq 0}}^{N} w_j I^0(\mu_j; \tau^\perp)\left[\sum_{\ell=0}^{2M-1'}(2\ell+1)\frac{g_{\tau^\perp}^\ell}{2}\Lambda_\ell^0(\mu)\Lambda_\ell^0(\mu_j)\right]\right\}$$

Boundary Conditions $$I^0(+\mu; \tau_g^\perp) = \text{constant} > 0;$$

$$I^0(-\mu_i; 0) = 0.$$

As this equation illustrates, the radiative transport problem that must be solved to calculate $t_{emb\_dif}^{obs \to gnd}$ is identical to the problem solved for the $t_{diffuse}^{sun \to gnd}$ calculation, Eq. (66), except that the upwelling radiance, $I^0(+\mu^{gnd \to obs}; \tau^\perp)$ is determined within the medium, not at its upper boundary. [The equations also differ in that Eq. (66) is solved for the solar cosine $\mu^{sun}$, while Eq. (69) is solved for the view cosine $\mu^{gnd \to obs}$].

The calculation of spherical albedo, the solar path diffuse transmittance and the view angle medium-embedded diffuse transmittance by DISORT has been streamlined as part of the IMPROVEMENTS TO MODTRAN4™. DISORT provides an option to calculate spherical albedo and diffuse transmittance in a dedicated run of the model. The IMPROVEMENTS TO MODTRAN4™ use DISORT to calculate both the line-of-sight (LOS) scattered radiance contributions and the atmospheric correction data. These two calculations required the same sets of Legendre polynomials and atmospheric layer Eigenvalues and Eigenvectors; they differ in their constants of integration because of differing boundary conditions. DISORT in IMPROVEMENTS TO MODTRAN4™ has been modified to generate both the LOS and atmospheric correction data (including the medium-embedded diffuse transmittance) in a single call with redundant computations eliminated. With a vector optimized compiler, the extra computational effort required to generate the atmospheric correction data during a LOS scattered radiance calculation only amounts to a few percent of the overall time.

Surface Moisture

Atmospheric water vapor retrievals from down-looking visible and infrared imaging sensor data are adversely impacted by surface droplets and/or embedded liquid water on otherwise dry backgrounds, as with dew or within chlorophyll structures like the leaves of a forested canopy. The water vapor retrieval algorithms typically assume the background and atmospheric water signatures are uncorrelated; this is untrue if the background contains liquid water. This spectral correlation of the surface signature with atmospheric water also presents a problem for viewing against extended water body backgrounds, as in littoral scenes. The details of the radiation transport (RT) in the background underwater scenario is considerably different from embedded water or water droplet scenario. This section describes approaches recently implemented within IMPROVEMENTS TO MODTRAN4™ for dealing with both situations.

Embedded Water Attenuation Model

The IMPROVEMENTS TO MODTRAN4™ embedded water or moisture attenuation model incorporates the effects of the liquid water extinction directly into its surface spectral reflectance model. For a dry background, MODTRAN™ parameterizes surface reflectance via a spectral grid $\lambda_i$ (i=0, ..., N) of bidirectional reflectance distribution functions (BRDFs), $f_i(\Omega_v, \Omega_s)$ and their angularly integrated products. These reflectance products include (a) $\rho_i(\Omega_v)$, the surface spectral directional reflectivities in the view solid angle direction, $\Omega_v \equiv (\mu_v, \phi_v)$; (b) $\rho_i(\Omega_s)$, the surface spectral directional reflectivities in the source solid angle direction, $\Omega_s \equiv (\mu_s, \phi_s)$; and (c) $\alpha_i$, the double hemisphere integrated surface spectral albedos:

$$\rho_i(\Omega_v) \equiv \int_{2\pi} f_i(\Omega_v, \Omega_s)\mu_s d\Omega_s; \quad (70)$$

$$\rho_i(\Omega_s) \equiv \int_{2\pi} f_i(\Omega_v, \Omega_s)\mu_v d\Omega_v;$$

$$\alpha_i \equiv \frac{1}{\pi}\int_{2\pi}\rho_i(\Omega_v)\mu_v d\Omega_v = \frac{1}{\pi}\int_{2\pi}\rho_i(\Omega_s)\mu_s d\Omega_s.$$

As indicated above, the solid angles $\Omega_v$ and $\Omega_s$ have two components: the cosine of a zenith angle $\mu$ and an azimuth angle $\phi$.

The embedded water attenuation model uses a single semi-empirical depth parameter, D, to incorporate liquid water attenuation into the surface spectral reflectance terms:

$$f_i(\Omega_v, \Omega_s; D) \equiv e^{-b_i D/\mu_v} f_i(\Omega_v, \Omega_s) e^{-b_i D/\mu_s}; \quad (71)$$

$$\rho_i(\Omega_v; D) \equiv \int_{2\pi} f_i(\Omega_v, \Omega_s; D)\mu_s d\Omega_s$$

$$= e^{-b_i D/\mu_v}\left[\int_{2\pi} f_i(\Omega_v, \Omega_s)e^{-b_i D/\mu_s}\mu_s d\Omega_s\right];$$

$$\rho_i(\Omega_s; D) \equiv \int_{2\pi} f_i(\Omega_v, \Omega_s; D)\mu_v d\Omega_v$$

$$\equiv \left[\int_{2\pi} e^{-b_i D/\mu_v} f_i(\Omega_v, \Omega_s)\mu_v\right]e^{-b_i D/\mu_s};$$

$$\alpha_i(D) \equiv \frac{1}{\pi}\int_{2\pi}\rho_i(\Omega_v; D)\mu_v d\Omega_v$$

$$= \frac{1}{\pi}\int_{2\pi}\rho_i(\Omega_s; D)\mu_s d\Omega_s.$$

In these definitions, $b_i$ is the liquid water spectral extinction coefficient (1/m) at spectral wavelength $\lambda_i$. The extinction coefficients are computed as the sum of absorption $b_i^{abs}$ and scattering $b_i^{scat}$ terms, FIG. 6. The absorption coefficients $b_i^{abs}$ are derived from the Segelstein spectral complex refractive index tables. Smith and Baker scattering coefficient $b_i^{scat}$ data has been fit to a simple power law expression:

$$b_\lambda^{scat} = \frac{1.12926 \times 10^{-4}/m}{[\lambda(\mu m)]^{4.32}}, \quad (72)$$

In this expression, $\lambda$ is the spectral wavelength in microns. As evidenced by FIG. 7, the scattering contribution to the overall extinction is negligible for wavelengths above ~1 μm, and extrapolation of the data is inconsequential.

Since MODTRAN™ only needs the BRDF and directional reflectivities values at the solar and (downward) viewing angles, a generally coarse spectral grid of values are computed up front, i.e., before the primary MODTRAN spectral loop. For the dry surface, the reflectance quantities are then linearly interpolated in wavelength, as needed:

$$f_\lambda(\Omega_v, \Omega_s) = \left(\frac{\lambda_i - \lambda}{\lambda_i - \lambda_{i-1}}\right) f_{i-1}(\Omega_v, \Omega_s) + \left(\frac{\lambda - \lambda_{i-1}}{\lambda_i - \lambda_{i-1}}\right) f_i(\Omega_v, \Omega_s); \quad (73)$$

$$[\lambda_{i-1} \leq \lambda \leq \lambda_i]$$

$$\rho_\lambda(\Omega_v) = \left(\frac{\lambda_i - \lambda}{\lambda_i - \lambda_{i-1}}\right)\rho_{i-1}(\Omega_v) + \left(\frac{\lambda - \lambda_{i-1}}{\lambda_i - \lambda_{i-1}}\right)\rho_i(\Omega_v);$$

$$\rho_\lambda(\Omega_s) = \left(\frac{\lambda_i - \lambda}{\lambda_i - \lambda_{i-1}}\right)\rho_{i-1}(\Omega_s) + \left(\frac{\lambda - \lambda_{i-1}}{\lambda_i - \lambda_{i-1}}\right)\rho_i(\Omega_s);$$

$$\alpha_\lambda = \left(\frac{\lambda_i - \lambda}{\lambda_i - \lambda_{i-1}}\right)\alpha_{i-1} + \left(\frac{\lambda - \lambda_{i-1}}{\lambda_i - \lambda_{i-1}}\right)\alpha_i.$$

However, the coarse wavelength grids commonly used for the surface description will not capture the spectral structure of the liquid water absorption, FIG. 7.

Incorporating the finer spectral dependence of the water absorption is straightforward for the BRDF term:

$$f_\lambda(\Omega_v, \Omega_s; D) \equiv e^{-b_\lambda D/\mu_v} f_\lambda(\Omega_v, \Omega_s) e^{-b_\lambda D/\mu_s} \quad (74)$$

$$= e^{-b_\lambda D/\mu_v}\left[\left(\frac{\lambda_i - \lambda}{\lambda_i - \lambda_{i-1}}\right) f_{i-1}(\Omega_v, \Omega_s) + \right.$$

$$\left.\left(\frac{\lambda - \lambda_{i-1}}{\lambda_i - \lambda_{i-1}}\right) f_i(\Omega_v, \Omega_s)\right] e^{-b_\lambda D/\mu_s}.$$

Modeling of the directional reflectivity and double hemisphere integrated albedo terms is more difficult because the angular integrations, which are preferentially performed in preprocessing, are spectrally dependent on the water absorption. The following approximation is introduced to compute the spectral directional reflectivities:

$$\rho_\lambda(\Omega_v; D) \equiv \int_{2\pi} f_\lambda(\Omega_v, \Omega_s; D)\mu_s d\Omega_s \quad (75)$$

$$= e^{-b_\lambda/\mu_v}\left[\left(\frac{\lambda_i - \lambda}{\lambda_i - \lambda_{i-1}}\right) f_{i-1}(\Omega_v, \langle\Omega_s\rangle_{i-1}) + \right.$$

$$\left.\left(\frac{\lambda - \lambda_{i-1}}{\lambda_i - \lambda_{i-1}}\right) f_i(\Omega_v, \langle\Omega_s\rangle_i)\right] \int_{2\pi} e^{-b_\lambda D/\mu_s} \mu_s d\Omega_s$$

$$\approx \left[\left(\frac{\lambda_i - \lambda}{\lambda_i - \lambda_{i-1}}\right) \frac{\rho_{i-1}(\Omega_v; D)}{2E_3(b_{i-1}D)e^{-b_{i-1}D/\mu_v}} + \right.$$

$$\left.\left(\frac{\lambda - \lambda_{i-1}}{\lambda_i - \lambda_{i-1}}\right) \frac{\rho_i(\Omega_v; D)}{2E_3(b_iD)e^{-b_iD/\mu_v}}\right] 2E_3(b_\lambda D)e^{-b_\lambda D/\mu_v},$$

where $$f_i(\Omega_v, \langle\Omega_s\rangle_i) \equiv \frac{\int_{2\pi} f_i(\Omega_v, \Omega_s)e^{-b_\lambda D/\mu_s}\mu_s d\Omega_s}{\int_{2\pi} e^{-b_\lambda D/\mu_s}\mu_s d\Omega_s} \quad (76)$$

$$\approx \frac{\int_{2\pi} f_i(\Omega_v, \Omega_s)e^{-b_iD/\mu_s}\mu_s d\Omega_s}{\int_{2\pi} e^{-b_iD/\mu_s}\mu_s d\Omega_s}$$

$$= \frac{\rho_i(\Omega_s; D)}{2\pi E_3(b_iD)e^{-b_iD/\mu_s}}$$

and $E_3(b_\lambda D)$ is the exponential integral of order 3:

$$2\pi E_3(b_\lambda D) \equiv 2\pi \int_1^\infty \frac{e^{-b_\lambda Dt}}{t^3} dt = \int_{2\pi} e^{-b_\lambda D/\mu}\mu d\Omega. \quad (77)$$

Here the mean value theorem is being invoked to pull $f_i(\Omega_v, \Omega_s)$ out of the integrand at $\Omega_s = \langle\Omega_s\rangle_i$ and $f_i(\Omega_v, \langle\Omega_s\rangle_i)$ is being approximated by a transmittance-weighted average at $\lambda = \lambda_i$. Thus, even though $f_i(\Omega_v, \langle\Omega_s\rangle_i)$ is actually defined as a spectrally varying quantity because of its dependence on the extinction coefficient $b_\lambda$, it is approximated by a spectrally independent quantity. This weighted average insures that $\rho_\lambda(\Omega_v; D)$ indeed equals the precomputed integral $\rho_i(\Omega_v; D)$ at the spectral grid point, $\lambda = \lambda_i$. Since the effective hemispheric transmittance equals twice the exponential integral [note that $2E_3(b_iD)|_{D=0}$ equals unity, as it should], a coefficient of 2 is included with each occurrence of the exponential integral in the final line of Eq. (75). With this expression for the directional reflectivity, the only integral that has to be computed on-the-fly spectrally is the exponential integral of order 3, and well established algorithms are readily available for this evaluation.

The double integral mean value theorem and the corresponding double path transmittance weighted average are used to derive an analogous expression for the spectral albedo:

$$\alpha_\lambda(D) \equiv \frac{1}{\pi}\int_{2\pi}\left[\int_{2\pi} f_\lambda(\Omega_v, \Omega_s; D)\mu_s d\Omega_s\right]\mu_v d\Omega_v \quad (78)$$

$$= \frac{1}{\pi}\left[\left(\frac{\lambda_i - \lambda}{\lambda_i - \lambda_{i-1}}\right) f_{i-1}(\langle(\Omega_v, \Omega_s)\rangle_{i-1}) + \right.$$

$$\left.\left(\frac{\lambda - \lambda_{i-1}}{\lambda_i - \lambda_{i-1}}\right) f_i(\langle(\Omega_v, \Omega_s)\rangle_i)\right]\left(\int_{2\pi} e^{-b_\lambda D/\mu}\mu d\Omega\right)^2$$

$$\approx \left[\left(\frac{\lambda_i - \lambda}{\lambda_i - \lambda_{i-1}}\right) \frac{\alpha_{i-1}(D)}{4E_3(b_{i-1}D)^2} + \right.$$

$$\left.\left(\frac{\lambda - \lambda_{i-1}}{\lambda_i - \lambda_{i-1}}\right) \frac{\alpha_i(D)}{4E_3(b_iD)^2}\right] 4E_3(b_\lambda D)^2,$$

where $$\frac{1}{\pi} f_i(\langle(\Omega_v, \Omega_s)\rangle_\lambda) \equiv \frac{\left[\int_{2\pi} f_i(\Omega_v, \Omega_s)e^{-b_\lambda D/\mu_s}\mu_s d\Omega_s\right]\mu_v d\Omega_v}{(\int_{2\pi} e^{-b_\lambda D/\mu}\mu d\Omega)^2} \quad (79)$$

$$\frac{1}{\pi}\int_{2\pi} e^{-b_\lambda D/\mu_v}$$

$$\approx \frac{\left[\int_{2\pi} f_i(\Omega_v, \Omega_s)e^{-b_iD/\mu_s}\mu_s d\Omega_s\right]\mu_v d\Omega_v}{(\int_{2\pi} e^{-b_iD/\mu}\mu d\Omega)^2}$$

$$= \frac{\alpha_i(D)}{4E_3(b_iD)^2}$$

Again, the mean value theorem allows that BRDF to be pulled out of the integrand, but $f_i$ is evaluated at a pair of solid angles, $(\Omega_s, \Omega_v) = \langle\Omega_s, \Omega_v\rangle_i$ for the surface albedo calculation.

In the preprocessing step, the $\rho_i(\Omega; D)$ of Eq. (75) and $\alpha_i(D)$ of Eq. (78) are computed by numerically integrating the BRDF; these integrals are divided by the spectral grid denominator terms [$2 E_3(b_iD) \exp(-b_iD/\mu)$ and $4 E_2(b_iD)^2$, respectively] and stored for use in the fine spectral resolution calculations. No numeric intergrations over the BRDF are performed during this band model spectral loop—only spectral interpolations and calculations of exponentials and exponential intergrals.

Flat Water Layer Model

The flat water layer model is quite distinct form the embedded layer model in that the liquid water is modeled as a layer that lies above a surface with specified reflectance properties. This introduces three effects in addition to the attenuation embedded water model:
- Fresnel transmittance and reflectance from the air/water interface;
- Snell's Law refraction across the interface; and
- Multiple reflections arising primarily from photons that impinge upon the underside of air/water interface at angles greater than the critical angle, i.e., the total internal reflections contribution.

Consider first the directly transmitted contribution, FIG. 7, part a, to the BRDF at $\lambda_i$, $f_i^{direct}(\Omega_v,\Omega_s;D;r_i)$, defined here as source photons that are
1. transmitted down through the water-air interface,
2. redirected according to Snell's Law refraction,
3. attenuated by water layer extinction along the straight downward path,
4. reflected by the underlying surface,
5. attenuated by water layer extinction along the straight upward path,
6. transmitted up through the water-air surface, and again
7. redirected according to Snell's Law refraction.

The water layer BRDF contribution has the following form $$f_i^{direct}(\Omega_v, \Omega_s; D; r_i) \equiv r_i^2 t_i(\theta_v', \theta_v) f_i(\Omega_v', \Omega_s'; D) t_i(\theta_s', \theta_s) r_i^{-2} \quad (80)$$
$$= t_i(\theta_v', \theta_v) f_i(\Omega_v', \Omega_s'; D) t_i(\theta_s', \theta_s),$$

where $$t(\theta', \theta) \equiv 1 - \frac{1}{2}\left(\frac{\sin^2(\theta' - \theta)}{\sin^2(\theta' + \theta)} + \frac{\tan^2(\theta' - \theta)}{\tan^2(\theta' + \theta)}\right); \quad (81)$$

$$r_i \equiv n(\lambda_i)/n'(\lambda_i)$$
$$\sin\theta' = r_i\sin\theta;$$
$$\mu'^2 = \cos^2\theta' = 1 - r_i^2(1 - \cos^2\theta) = (1 - r_i^2) + r_i^2\mu^2$$
$$\mu' d\Omega' = \mu' d\phi' d\mu' = r_i^2\mu d\phi d\mu = r_i^2\mu d\Omega.$$

In these equations, $r_i(<1)$ is the air-to-water index of refraction ratio. In the first line of Eq. (80), the $r_i^2$ and $r_i^{-2}$ terms equal the radiance decrease from the expanded solid angle and increase from the constricted solid angle, respectively, resulting from Snell's Law refraction; these terms cancel because the radiation both enters and exits the water. The $t(\theta',\theta)$ terms are the spectral grid Fresnel interface transmittances. Primes (') are used to indicate underwater angles.

Approximate approaches are used to model the initial above water Fresnel reflection and the multiple under water reflections. Since water bodies are seldom well represented as having a strictly flat surface, the Fresnel reflection is averaged over the full hemisphere of incident angles, $\theta_s$; this approximation smoothes out the large contributions that occur for the specular reflection geometry. The reflected underwater contributions are modeled by treating the upwelling radiation from below the water-air interface is nearly isotropic. The fraction of photons whose incident angle will exceed the critical angle is $(1-r_i^2)$. Additional photons are Fresnel reflected, but this contribution is small because the Fresnel transmittance is close to one for incident angles less than the critical angle. Thus, a fraction equal to $r_i^2$ of the upwelling flux penetrates the air-water interface, and $(1-r_i^2)$ is reflected.

The next question that must be answered is "what fraction of the photons reflected from the underside of the water-air interface will return to that interface?" This water layer bottom spherical albedo term is approximated by the double path attenuated water layer surface albedo $\alpha_i(D)$ of Eq. (71). Two somewhat compensating assumptions are made: (1) that the backscatter from within the water layer is relatively minor and (2) that the reflected downward flux is nearly isotropic even though the total internal reflections only occur for larger incident angles. Given these approximations, the flat water layer model BRDF is expressed as $$f_i(\Omega_v, \Omega_s; D; r_i) \approx t_i(\theta_v', \theta_v)r_i^2[\cdots]t_i(\theta_v', \theta_v) + \quad (82)$$
$$\frac{1}{\pi^2}\int_{2\pi}[1 - t_i(\theta_s', \theta_s)]\mu_s d\Omega_s$$
$$= \frac{r_i^2 f_i^{direct}(\Omega_v, \Omega_s; D; r_i)}{1 - (1 - r_i^2)\alpha_i(D)} + \frac{1}{\pi}\langle 1 - t_i(\theta_s', \theta_s)\rangle,$$

where $$[\cdots] \equiv \begin{bmatrix} f_i(\Omega_v', \Omega_s'; D) + \\ \int_{a\sin r_i<\theta'<\pi/2} f_i(\Omega_v', \Omega'; D)f_i(\Omega', \Omega_s'; D)\mu' d\Omega' + \\ \int_{a\sin r_i<\theta'<\pi/2} f_i(\Omega_v', \Omega'; D)\left(\int_{a\sin r_i\theta''<\pi/2} f_i(\Omega', \Omega_s''; D) f_i(\Omega'', \Omega_s'; D)\mu'' d\Omega''\right) \\ \mu' d\Omega' + \cdots \end{bmatrix} \quad (83)$$
$$\approx f_i(\Omega_v', \Omega_s'; D)[1 + (1-r_i^2)\alpha_i(D) + (1-r_i^2)^2\alpha_i^2(D) + \cdots]$$
$$= \frac{f_i(\Omega_v', \Omega_s'; D)}{1 - (1 - r_i^2)\alpha_i(D)}$$

and $$\langle 1 - t_i(\theta_s', \theta_s)\rangle \equiv 1 - \frac{1}{\pi}\int_{2\pi} t_i(\theta_s', \theta_s)\mu_s d\Omega_s \quad (84)$$

The first two terms in Eq. (83) are illustrated pictorially by FIGS. 7 part a and 7 part b, respectively; FIG. 7 part c depicts the remaining terms in the series.

To calculate of the flat water layer BRDF at an arbitrary wavelength, the underwater surface BRDF and the water layer attenuated surface albedo are spectrally interpolated, Eqs. (73) and (76), respectively:

$$f_\lambda(\Omega_v, \Omega_s; D; r_\lambda) \equiv \frac{r_\lambda^2 f_\lambda^{direct}(\Omega_v, \Omega_s; D; r_\lambda)}{1 - (1 - r_\lambda^2)\alpha_\lambda(D)} + \quad (85)$$
$$\frac{1}{\pi}\left(1 - \frac{1}{\pi}\int_{2\pi} t_\lambda(\theta_s', \theta_s)\mu_s d\Omega_s\right)$$
$$= \frac{r_\lambda^2 t_\lambda(\theta_v', \theta_v)f_\lambda(\Omega_v', \Omega_s'; D)t_\lambda(\theta_s', \theta_s)}{1 - (1 - r_\lambda^2)\alpha_\lambda(D)} +$$
$$\frac{1}{\pi}\langle 1 - t_\lambda(\theta_s', \theta_s)\rangle.$$

The angularly averaged Fresnel reflection, $<1-t_\lambda(\theta'_s, \theta_s)>$, is solely a function of the air-to-water refractive index ratio, $r_\lambda$. This ratio falls in a range from 1.09 to 1.56 over the entire far ultra-violet through long-wave infrared spectral region from 0.2 to 32 µm; with this limited range, the angularly averaged Fresnel reflection can be accurately fit to a quadratic in $r_\lambda$ for efficient computation:

$$\langle 1-t_\lambda(\theta'_s,\theta_s)\rangle \approx -0.3421 + 0.5033 r_\lambda - 0.1532 r_\lambda^2 \quad (86)$$

The spectral grid directional reflectance in the view direction, $\rho_i(\Omega_v;D;r_i)$, and surface albedo, $\alpha_i(D;r_i)$, for the flat water layer model are defined by the single and double hemisphere integrated BRDF, respectively:

$$\rho_i(\Omega_v; D; r_i) \equiv \int_{2\pi} f_i(\Omega_v, \Omega_s; D; r_i)\mu_s d\Omega_s \quad (87)$$

$$= \frac{t_i(\theta'_v, \theta_v) r_i^2}{1-(1-r_i^2)\alpha_i(D)} \int_0^1 t_i(\theta'_s, \theta_s)$$

$$\int_0^{2\pi} f_i(\Omega'_v, \Omega'_s; D) d\phi_s \mu_s d\mu_s +$$

$$\langle 1 - t_i(\theta'_s, \theta_s)\rangle$$

$$\equiv \tilde\rho_i(\Omega_v; D; r_i) + \langle 1 - t_i(\theta'_s, \theta_s)\rangle;$$

$$\alpha_i(D; r_i) = \frac{1}{\pi} \int_{2\pi} \left[\int_{2\pi} f_i(\Omega_v, \Omega_s; D; r_i)\mu_s d\Omega_s\right]\mu_v d\Omega_v \quad (88)$$

$$= \frac{1}{\pi}\int_{2\pi} \rho_i(\Omega_v; D; r_i)\mu_v d\Omega_v;$$

where $\tilde\rho$ is defined as the water leaving radiance contribution to $\rho$. Since the BRDF is defined for the underwater surface, it is easiest to perform numerical integrations using the underwater source and view angles. A change of variables via Eq. (81) leads to the following expressions:

$$\rho_i(\Omega_v; D; r_i) = \frac{1}{r_i^2}\int_{\sqrt{1-r_i^2}}^1 \int_0^{2\pi} f_i(\Omega_v, \Omega_s; D; r_i) d\phi'_s \mu'_s d\mu'_s, \quad (89)$$

$$\alpha_i(D; r_i) = \frac{1}{\pi r_i^4}\int_{\sqrt{1-r_i^2}}^1 \int_0^{2\pi}$$

$$\left[\int_{\sqrt{1-r_i^2}}^1 \int_0^{2\pi} f_i(\Omega_v, \Omega_s; D; r_i) d\phi'_s \mu'_s d\mu'_s\right] d\phi'_v \mu'_v d\mu'_v$$

$$= \frac{1}{\pi r_i^2}\int_{\sqrt{1-r_i^2}}^1 \int_0^{2\pi} \rho_i(\Omega_v; D; r_i) d\phi'_v \mu'_v d\mu'_v.$$

In these expressions, the angular integral domain itself is spectrally dependent.

For the calculation of directional reflectivity at an arbitrary spectral point, $\rho_\lambda(\Omega';D;r_\lambda)$, the spectrally slowly varying BRDF assumption used in the embedded water attenuation model is replaced with the ansatz that the product of the BRDF with the Fresnel interface transmittance is spectrally slowly varying:

$$[ft]_\lambda(\Omega'_v, \Omega'_s) \equiv f_\lambda(\Omega'_v, \Omega'_s) t_\lambda(\theta'_s, \theta_s) \quad (90)$$

$$\approx \left(\frac{\lambda_i - \lambda}{\lambda_i - \lambda_{i-1}}\right) f_{i-1}(\Omega'_v, \Omega'_s) t_{i-1}(\theta'_s, \theta_s) +$$

$$\left(\frac{\lambda - \lambda_{i-1}}{\lambda_i - \lambda_{i-1}}\right) f_i(\Omega'_v, \Omega'_s) t_i(\theta'_s, \theta_s)$$

-continued $$= \left(\frac{\lambda_i - \lambda}{\lambda_i - \lambda_{i-1}}\right)[ft]_{i-1}(\Omega'_v, \Omega'_s)$$

$$\left(\frac{\lambda - \lambda_{i-1}}{\lambda_i - \lambda_{i-1}}\right)[ft]_i(\Omega'_v, \Omega'_s).$$

As illustrated in FIG. 8, the liquid water index of refraction only varies between 1.09 and 1.56 for essentially the entire MODTRAN spectral range; however, there are relatively dramatic variations near the 3.0 µm and 6.1 µm liquid water vibrational fundamental bands and in the heart of the pure rotational bands (>10 µm). Within these spectral sub-regions, it is best if the user specifies the sub-surface BRDF on a relative fine spectral grid to protect against inaccurate interpolations of the Fresnel transmittance.

Once again, the mean value theorem is invoked; here it is used to extract the $[ft]_\lambda$ product out of the spectral directional reflectivity angular integration:

$$\tilde\rho_\lambda(\Omega_v; D; r_i) \equiv \frac{1}{r_\lambda^2}\int_{\sqrt{1-r_\lambda^2}}^1 \int_0^{2\pi} f_\lambda(\Omega_v, \Omega_s; D; r_\lambda)\mu'_s d\phi'_s d\mu'_s - \quad (91)$$

$$\langle 1 - t_\lambda(\theta'_s, \theta_s)\rangle$$

$$= \frac{t_\lambda(\theta'_v, \theta_v)}{1-(1-r_\lambda^2)\alpha_\lambda(D)}\int_{\sqrt{1-r_\lambda^2}}^1 \int_0^{2\pi} f_\lambda(\Omega'_v, \Omega'_s; D)$$

$$t_\lambda(\theta'_s, \theta_s)\mu'_s d\phi'_s d\mu'_s$$

$$= \frac{t_\lambda(\theta'_v, \theta_v)e^{-b_\lambda D/\mu_v}}{1-(1-r_\lambda^2)\alpha_\lambda(D)}[ft]_\lambda(\Omega'_v, \langle\Omega'_s\rangle_\lambda)$$

$$\int_{\sqrt{1-r_\lambda^2}}^1 \int_0^{2\pi} e^{-b_\lambda D/\mu'_s}\mu'_s d\phi'_s d\mu'_s.$$

Like the full hemisphere water layer transmittance, Eq. (77), the conical water layer transmittance of Eq. (91) is a function of elliptical integrals, but with added complexity resulting from the restricted domain:

$$\int_{\sqrt{1-r_\lambda^2}}^1 \int_0^{2\pi} e^{-b_\lambda D/\mu'_s}\mu'_s d\phi'_s d\mu'_s = \quad (92)$$

$$2\pi\left[E_3(b_\lambda D) - (1-r_\lambda^2)E_3\left(b_\lambda D/\sqrt{1-r_\lambda^2}\right)\right]$$

The spectral grid components of $[ft]_\lambda$ are approximated by the conical water layer transmittance weighted average evaluated at the spectral grid points:

$$e^{-b_\lambda S/\mu_v}[ft]_i(\Omega'_v, \langle\Omega'_s\rangle_\lambda) \approx \quad (93)$$

$$\frac{\int_{\sqrt{1-r_i^2}}^1 \left[\int_0^{2\pi} f_i(\Omega'_v, \Omega'_s; D) d\phi'_s\right] t_i(\theta'_s, \theta_s)\mu'_s d\mu'_s}{2\pi\left[E_3(b_i D) - (1-r_i^2)E_3\left(b_i D/\sqrt{1-r_i^2}\right)\right]}$$

By first substituting Eqs. (90) and (92) into the expression for the spectral directional reflectivity, Eq. (91); then approximating the $[ft]_i$ terms according to Eq. (93); and finally incorporating the spectral grid directional reflectivity expression, Eq. (89), the spectral directional reflectivity in the view (source) direction has the following form:

$$\frac{\tilde{p}_\lambda(\Omega_v;D;r_\lambda)}{C_\lambda^{(\rho)}(\Omega_v;D;r_\lambda)} \approx \left(\frac{\lambda_i-\lambda}{\lambda_i-\lambda_{i-1}}\right)\frac{\tilde{p}_{i-1}(\Omega_v;D;r_{i-1})}{C_{i-1}^{(\rho)}(\Omega_v;D;r_{i-1})} + \quad (94)$$
$$\left(\frac{\lambda-\lambda_{i-1}}{\lambda_i-\lambda_{i-1}}\right)\frac{\tilde{p}_i(\Omega_v;D;r_i)}{C_i^{(\rho)}(\Omega_v;D;r_i)};$$
$$\frac{\tilde{p}_\lambda(\Omega_s;D;r_\lambda)}{C_\lambda^{(\rho)}(\Omega_s;D;r_\lambda)} \approx \left(\frac{\lambda_i-\lambda}{\lambda_i-\lambda_{i-1}}\right)\frac{\tilde{p}_{i-1}(\Omega_s;D;r_{i-1})}{C_{i-1}^{(\rho)}(\Omega_s;D;r_{i-1})} +$$
$$\left(\frac{\lambda-\lambda_{i-1}}{\lambda_i-\lambda_{i-1}}\right)\frac{\tilde{p}_i(\Omega_s;D;r_i)}{C_i^{(\rho)}(\Omega_s;D;r_i)},$$

where the denominator $C_\lambda^{(\rho)}$ is a transmittance enhanced by multiple reflections $$C_\lambda^{(\rho)}(\Omega_{v,s};D;r_\lambda) \equiv \qquad (95)$$
$$\frac{t_\lambda(\theta'_{v,s},\theta_{v,s})\left[E_3(b_\lambda D)-(1-r_\lambda^2)E_3\left(b_\lambda D/\sqrt{1-r_\lambda^2}\right)\right]}{1-(1-r_\lambda^2)\alpha_\lambda(D)}.$$

A completely analogous procedure is used to define the flat water layer spectral double hemisphere albedo. The water leaving contribution to the spectral grid value has the following fully expanded form:

$$\tilde{\alpha}_i(D;r_i) \equiv \alpha_i(D;r_i) + \langle 1-t_\lambda(\theta'_s,\theta_s)\rangle \qquad (96)$$
$$= \frac{\left[\int_{\sqrt{1-r_i^2}}^{1}e^{-b_iD/\mu'_s}t_i(\theta'_v,\theta_v)f_i(\Omega'_v,\Omega_v)t_i(\theta'_s,\theta_s)d\phi'_s\mu'_sd\mu'_s\right]d\phi'_v\mu'_vd\mu'_v}{\pi r_i^2[1-(1-r_i^2)\alpha_i(D)]}$$

Spectral interpolations are performed over a triple product, the BRDF with the Fresnel transmittance in both the view and source directions:

$$[tft]_\lambda(\Omega'_v,\Omega'_s) \equiv t_\lambda(\theta'_v,\theta_v)f_\lambda(\Omega'_v,\Omega'_s)t_\lambda(\theta'_s,\theta_s) \qquad (97)$$
$$\approx \left(\frac{\lambda_i-\lambda}{\lambda_i-\lambda_{i-1}}\right)t_{i-1}(\theta'_v,\theta_v)f_{i-1}(\Omega'_v,\Omega'_s)t_{i-1}(\theta'_s,\theta_s) +$$
$$\left(\frac{\lambda-\lambda_{i-1}}{\lambda_i-\lambda_{i-1}}\right)t_i(\theta'_v,\theta_v)f_i(\Omega'_v,\Omega'_s)t_i(\theta'_s,\theta_s).$$

The final expression for the flat water layer spectral albedo contains the double path conical transmittance enhanced by multiple reflections:

$$\frac{\tilde{\alpha}_\lambda(D;r_\lambda)}{C_\lambda^{(\alpha)}(D;r_\lambda)} \approx \left(\frac{\lambda_i-\lambda}{\lambda_i-\lambda_{i-1}}\right)\frac{\tilde{\alpha}_{i-1}(D;r_{i-1})}{C_{i-1}^{(\alpha)}(D;r_{i-1})} + \left(\frac{\lambda-\lambda_{i-1}}{\lambda_i-\lambda_{i-1}}\right)\frac{\tilde{\alpha}_i(D;r_i)}{C_i^{(\alpha)}(D;r_i)}, \qquad (98)$$

where $$C_\lambda^{(\alpha)}(D;r_\lambda) \equiv \frac{\left[E_3(b_\lambda D)-(1-r_\lambda^2)E_3\left(b_\lambda D/\sqrt{1-r_\lambda^2}\right)\right]^2}{r_\lambda^2[1-(1-r_\lambda^2)\alpha_k(D)]}. \qquad (99)$$

During MODTRAN™ pre-processing for the flat water layer model, the BRDF is numerically integrated to compute the spectral grid point directional reflectivities $\rho_i(\Omega;D;r_i)$ and albedos $\alpha_i(D;r_i)$. These values are stored after being divided by transmittances terms $C_\lambda^{(\rho)}$ and $C_\lambda^{(\alpha)}$, respectively. No numerical integration of the BRDF is required at the finer spectral resolution of the MODTRAN™ band model. The flat water layer model calculations performed at this finer resolution are quick and straightforward; they include calculation of the liquid water and air refractive indices, calculation of the Fresnel transmittance, calculation of the elliptical integrals and calculation of the spectral interpolations.

Special Cases

It is of interest to examine both the embedded water attenuation and the flat water layer models for the scenario in which the underlying BRDF is Lambertian:

$$f_i^{Lamb}(\Omega_v,\Omega_s) \equiv \alpha_i/\pi. \qquad (100)$$

For the embedded water attenuation model, substitution into Eq. (71) gives the following expressions:

$$f_i^{Lamb}(\Omega_v,\Omega_s;D) \equiv \frac{\alpha_i}{\pi}e^{-b_iD/\mu_s}; \qquad (101)$$
$$\rho_i^{Lamb}(\Omega_v;D) \equiv 2\alpha_i E_3(b_iD)e^{-b_iD/\mu_v};$$

-continued
$$\rho_i^{Lamb}(\Omega_s;D) \equiv 2\alpha_i E_3(b_iD)e^{-b_iD/\mu_s};$$
$$\alpha_i^{Lamb}(D) \equiv 4\alpha_i E_3(b_iD)^2.$$

Not surprisingly, as the depth D approaches zero, the reflectances each approach the Lambertian limit.

The flat water layer model is more complex because of the Fresnel interface and the multiple underwater reflections. Combining the results of Eq. (101), the definition from Eq. (90), and the BRDF expression of Eq. (82) gives $$f_i^{Lamb}(\Omega_v,\Omega_s;D;r_i) \equiv \frac{\alpha_i}{\pi}\left(\frac{r_i^2 t_i(\theta'_s,\theta_s)t_i(\theta'_v,\theta_v)e^{-b_iD/\mu'_v}e^{-b_iD/\mu'_s}}{1-4\alpha_i(1-r_i^2)E_3(b_iD)^2}\right). \qquad (102)$$

To obtain approximate analytic expressions for the integrated reflectance terms, the additional simplification is made that the Fresnel transmittance within the angular integrands is unity for zenith angles below the critical angle, $\sin\theta' < r_i$:

$$t(\theta',\theta) \approx \begin{cases} 1 & \text{for }\sin\theta' < r_i \\ 0 & \text{for }\sin\theta' > r_i \end{cases}. \qquad (103)$$

For the Lambertian limit, Eq. (89) becomes $$\rho_i^{Lamb}(\Omega_v; D; r_i) \approx \frac{2\alpha_i e^{-b_i D/\mu_v'} t_i(\theta_v', \theta_v)\left[E_3(b_i D) - (1-r_i^2)E_3\left(b_i D/\sqrt{1-r_i^2}\right)\right]}{1 - 4\alpha_i(1-r_i^2)E_3(b_i D)^2},$$

$$\alpha_i^{Lamb}(D; r_i) \approx \frac{4\alpha_i\left[E_3(b_i D) - (1-r_i^2)E_3\left(b_i D/\sqrt{1-r_i^2}\right)\right]^2}{r_i^2[1 - 4\alpha_i(1-r_i^2)E_3(b_i D)^2]}.$$  (104)

As the depth of the water goes to zero, these reflectance simplify even further:

$$f_i^{Lamb}(\Omega_v, \Omega_s; 0; r_i) \equiv \frac{\alpha_i}{\pi}\left(\frac{r_i^2 t_i(\theta_s', \theta_s) t_i(\theta_v', \theta_v)}{1 - \alpha_i(1-r_i^2)}\right),$$  (105)

$$\rho_i^{Lamb}(\Omega_v; 0; r_i) \approx \frac{\alpha_i t_i(\theta_v', \theta_v) r_i^2}{1 - \alpha_i(1-r_i^2)},$$

$$\alpha_i^{Lamb}(0; r_i) \approx \frac{\alpha_i r_i^2}{1 - \alpha_i(1-r_i^2)}.$$

If one furthers considers the limit of a perfect Lambertian reflector, $\alpha_i=1$, and the Fresnel transmittances are set to one, the Lambertian limit is obtained. The Lambertian limit is also obtained for a black ($\alpha_i=0$) surface. However, Eq. (105) does not reduce to the Lambertian limit for grey bodies. In particular, if the reflectance is 50% ($\alpha_i=\frac{1}{2}$), then the albedo equals $r_i^2/(1+r_i^2)$. For water, this ratio is closer to one-third than to one-half.

| List of Symbols | |
|---|---|
| $B_\nu(T)$ | Planck Blackbody Spectral Emission at Temperature T [W cm$^{-2}$ sr$^{-1}$/cm$^{-1}$]. |
| $b_\nu(s)$ | Spectral Extinction Coefficient at Path Length s [cm$^{-1}$]. |
| $b_{\nu,i}$ | Spectral Extinction Coefficient for Species i [cm$^{-1}$]. |
| $b_\nu^{abs}(s)$ | Spectral Absorption Coefficient at Path Length s [cm$^{-1}$]. |
| $b_{\nu,i}^{abs}(s)$ | Spectral Absorption Coefficient at Path Length s for Species i [cm$^{-1}$]. |
| $b_\nu^{sct}(s)$ | Spectral Scattering Coefficient at Path Length s [cm$^{-1}$]. |
| $b_{\nu,i}^{sct}(s)$ | Spectral Scattering Coefficient at Path Length s for Species i [cm$^{-1}$]. |
| $C_\nu^{CO2}$ | Spectral CO$_2$ Continuum Parameter [(cm$^2$/mol)/cm$^{-1}$]. |
| $C_\nu^{H2O\,foreign}$ | Spectral Foreign-Broadened H$_2$O Continuum Parameter [(cm$^2$/mol)/cm$^{-1}$]. |
| $C_\nu^{H2O\,self}$ | Spectral Self-Broadened H$_2$O Continuum Parameter [(cm$^2$/mol)/cm$^{-1}$]. |
| $C_{jp}^m$ | Plane-Parallel RTE Homogeneous Problem Constants of Integration. |
| c | Speed of Light in a vacuum (2.9979246E+10 cm/sec). |
| $D(r_c)$ | Offset of Spectral Bin Center [cm$^{-1}$]. |
| $F_\nu^{sun}$ | Top-Of-Atmosphere (TOA) Spectral Solar Irradiance [W cm$^{-2}$/cm$^{-1}$]. |
| $F_\nu^\downarrow(s)$ | Downward Spectral Diffuse Flux at Path Length s [W cm$^{-2}$/cm$^{-1}$]. |
| $F^+(\tau^\downarrow)$ | Upward Spectral Total Flux at Vertical Optical Depth $\tau^\downarrow$ [W cm$^{-2}$/cm$^{-1}$]. |
| $F^-(\tau^\downarrow)$ | Downward Spectral Total Flux at Vertical Optical Depth $\tau^\downarrow$ [W cm$^{-2}$/cm$^{-1}$]. |
| f | Delta-M Method Separation Parameter. |
| $f_\nu(\gamma_c, \gamma_d)$ | Voigt Spectral Line-Shape Function [cm]. |
| $f_\nu(\Omega_s, \Omega'_s; s)$ | Ground BRDF for Outgoing $\Omega_s$ and Incoming $\Omega'_s$ Angles at Path Length s [sr$^{-1}$]. |
| $f^m(\mu; -\mu')$ | $m^{th}$ Azimuth Moment of the Ground BRDF [sr$^{-1}$]. |
| $G_{jp}^m$ | Plane-Parallel RTE Homogeneous Problem Eigenvectors [W cm$^{-2}$sr$^{-1}$/cm$^{-1}$]. |
| $g_{\tau\downarrow}^\lambda$ | Scattering Phase Function $\lambda^{th}$ Legendre Moment at Vertical Optical Depth $\tau^\downarrow$. |
| $g'^\lambda_{\tau\downarrow}$ | Delta-M Scattering Phase Function $\lambda^{th}$ Legendre Moment at Vertical Optical Depth $\tau^\downarrow$. |
| $g_p^\lambda$ | Scattering Phase Function $\lambda^{th}$ Legendre Moment Averaged over Layer p. |
| $H_{s'}$ | Above Sea Level Altitude at Path Length s' [km]. |
| $H_{(p)}$ | Above Sea Level Altitude at Profile Level p [km]. |
| $h_{s'}^p$ | Altitude Interpolation Fraction at Path Length s' for Atmospheric Layer p. |
| $I_n$ | Modified Bessel Function of order n. |
| $I_\nu(\Omega_s; s)$ | Spectral Radiant Intensity at Path Length s Along the $\Omega_s$ Direction [W cm$^{-2}$sr$^{-1}$/cm$^{-1}$]. |
| $I^m(\mu; \tau^\downarrow)$ | $m^{th}$ Azimuth Moment of the Plane-Parallel Atmosphere Spectral Radiant Intensities in Direction $\mu$ at Vertical Optical Depth $\tau^\downarrow$ [W cm$^{-2}$sr$^{-1}$/cm$^{-1}$]. |
| $I_p^m(\mu; \tau^\downarrow)$ | Plane-Parallel Spectral Radiant Intensities in Layer p [W cm$^{-2}$sr$^{-1}$/cm$^{-1}$]. |
| i | Species (Molecular or Particulate) Index. |
| i | Gaussian Moment Index. |
| j | Spectral Sub-Bin Index. |
| j | Gaussian Moment Index of Incoming Scattered or Reflected Radiation. |
| $J_\nu(\Omega_s; s)$ | Spectral Source Function at Path Length s Along the $\Omega_s$ Direction [W cm$^{-2}$sr$^{-1}$/cm$^{-1}$]. |
| k | Boltzmann constant (1.3807E−16 erg/K). |
| k | Molecular Index. |
| $k_{jp}^m$ | Eigenvalues of the Plane-Parallel RTE Homogeneous Problem. |
| L | Total Number of Atmospheric Layers. |
| l | Molecular Transition Index. |

-continued

List of Symbols

| | |
|---|---|
| $\lambda$ | Legendre Moment Index. |
| M | Spectral Band Index. |
| $\overline{M}$ | Effective Band Value Index. |
| M | One More Than the Total Number of Azimuth Moments. |
| m | Molecular Mass [g/molecule]. |
| m | Azimuth Moment Index. |
| N | Number of Spectral Sub-Interval in a Spectral Band. |
| N | Number of DISORT Streams in each Hemisphere. |
| $n_v(h)$ | Index of Refraction at Spectral Frequency v and Altitude h. |
| n | Line Number Band Model Parameter. |
| $\overline{n}$ | Curtis-Godson Path Averaged Line Number Band Model Parameter. |
| P | Pressure [Atm]. |
| $P_0$ | Standard Pressure [1 Atm]. |
| $\overline{P}_{\Delta s}$ | Path Segment Effective Pressure [Atm]. |
| $\overline{P}_s^k$ | Effective Pressure of Solar Illumination Path to s for Molecule k [Atm]. |
| $P_n$ | Integrals Used in the Definition of the $V_n$ Fourier Coefficients. |
| $P_\lambda(\mu)$ | $\lambda^{th}$ Legendre Polynomial at Cosine Zenith $\mu$. |
| p | Molecular Transition Index. |
| p | LOS Segment Index. |
| p | Layer or Level Index for Stratified Atmosphere. |
| $p(\Theta;\tau^\downarrow)$ | Spectral Scattering Phase Function for Scattering Angle $\Theta$ at Nadir Optical Depth $\tau^\downarrow$. |
| $p'(\Theta;\tau^\downarrow)$ | Delta-M Spectral Scattering Phase Function for Scattering Angle $\Theta$ at Nadir Optical Depth $\tau^\downarrow$. |
| $p_v(\Omega_s,\Omega'_s;s)$ | Spectral Scattering Phase Function for Outgoing and Incoming Angles $\Omega_s$ and $\Omega'_s$ at Path Length s [sr$^{-1}$]. |
| $p_{v,i}(\Omega_s,\Omega'_s;s)$ | Spectral Scattering Phase Function of Species i for Outgoing and Incoming Angles $\Omega_s$ and $\Omega'_s$ at Path Length s [sr$^{-1}$]. |
| $R_e$ | Radius of the Earth [km]. |
| $r_c$ | Ratio of Collision (Lorentz) Half-Width to Spectral Bin Width. |
| S | Molecular Line Strength [cm$^{-2}$/atm] |
| s | Full Path Length [cm]. |
| s' | Partial Path Length [cm]. |
| T | Temperature [K]. |
| $T_0$ | Standard Temperature [273.15 K]. |
| $\overline{T}_{\Delta s}$ | Path Segment Effective Temperature [K]. |
| $\overline{T}_s^k$ | Effective Temperature of Solar Illumination Path to s for Molecule k [K]. |
| $t_v(s)$ | Spectral Extinction Transmittance to Path Length s. |
| $t_k^{cen}$ | Molecular Transmittance from Line Center Absorption. |
| $t_k^{tail}$ | Molecular Transmittance from Line Tail Absorption. |
| $t_k^{coat}$ | Molecular Transmittance from Line Continuum Absorption. |
| $t_v^{abs}(s)$ | Spectral Absorption Transmittance to Path Length s. |
| $t_v^{sct}(s)$ | Spectral Scattering Transmittance to Path Length s. |
| U | Path Column Density Corresponding to a Transmittance of 1/e [Atm cm]. |
| u | Path Column Density [Atm cm]. |
| $V_n$ | Fourier Expansion Coefficients Used in the Modified Bessel Function Expansion of the Voigt Line Tail Equivalent Width. |
| $W^{sl}$ | Finite-Bin Equivalent Width (EW) of a Single Voigt Line [cm$^{-1}$] |
| $W_\Delta$ | Voigt Line Tail Equivalent Width [cm$^{-1}$]. |
| $w_i$ | Discrete Ordinate Gaussian Weight. |
| $x_n$ | Denominator $n^{th}$-Order Spectral Coefficient in Padé Approximant Fit to Line Tail Absorption Cross-Section [cm$^2$] |
| $Y_{0p}(\mu_i)$ | A Particular Solution to the Constant Thermal Source Plane-Parallel RTE Problem for Layer p [W cm$^{-2}$sr$^{-1}$/cm$^{-1}$]. |
| $Y_{1p}(\mu_i)$ | A Particular Solution to the Linear in Nadir Optical Depth Thermal Source Plane-Parallel RTE Problem for Layer p [W cm$^{-2}$sr$^{-1}$/cm$^{-1}$]. |
| $Z_p^m(\mu_i)$ | A Particular Solution to the Solar Source Plane-Parallel RTE Problem for Azimuth Moment m and Layer p [W cm$^{-2}$sr$^{-1}$/cm$^{-1}$]. |
| $\alpha_v(s)$ | Ground Surface Spectral Albedo intersected a distance s along the LOS. |
| $\delta_{m0}$ | Delta function (Equals 1 for m equal to 0; otherwise, equals 0). |
| $\delta_v$ | Normalized Spectral Bin Domain Variable ($-1$ to $+1$). |
| $\delta(x)$ | Dirac delta function. |
| $\gamma_c$ | Collision (Lorentz) half-width at half maximum [cm$^{-1}$]. |
| $\overline{\gamma}_c$ | Curtis-Godson Path Averaged Collision (Lorentz) half-width [cm$^{-1}$]. |
| $\gamma_c^0$ | Standard Pressure and Temperature Collision (Lorentz) half-width at half maximum [cm$^{-1}$]. |
| $\gamma_d$ | Doppler half-width at 1/e of the maximum [cm$^{-1}$]. |
| $\overline{\gamma}_d$ | Curtis-Godson Path Averaged Doppler half-width [cm$^{-1}$]. |
| $\epsilon_v(\Omega_s)$ | Ground Surface Spectral Directional Emissivity in Direction $\Omega_S$. |
| $\phi$ | Path Azimuth Angle. |
| $\kappa_{v,i}(s)$ | Species i Spectral Extinction Cross-Section at Path Length s [cm$^2$]. |
| $\kappa_{v,i}^{abs}(s)$ | Species i Spectral Absorption Cross-Section at Path Length s [cm$^2$]. |
| $\kappa_{v,i}^{sct}(s)$ | Species i Spectral Scattering Cross-Section at Path Length s [cm$^2$]. |
| $\kappa_n$ | Numerator $n^{th}$-Order Spectral Coefficient in Padé Approximant Fit to Line Tail Absorption Cross-Section [cm$^2$] |
| $\Lambda_\lambda^m(\mu)$ | Unit Normalized Associated Legendre Polynomial at Cosine Zenith $\mu$. |
| $\mu'$ | Cosine of the Path Zenith Angle at the Ground. |

-continued

List of Symbols

| | |
|---|---|
| $\mu_i$ | Discrete Ordinate Gaussian Abscissa. |
| $v$ | Spectral Frequency [cm$^{-1}$]. |
| $v_m$ | Spectral Bin Center Frequency [cm$^{-1}$]. |
| $\bar{v}$ | Calculation Spectral Domain Center Frequency [cm$^{-1}$]. |
| $\rho_i(s)$ | Density of Species i at Path Length s [number/cm$^3$]. |
| $\rho_v(\Omega_s)$ | Ground Surface Spectral Directional Reflectivity in Direction $\Omega_s$. |
| $\tau_v(s)$ | Spectral Extinction Optical Depth to Path Length s. |
| $\tau_v^{abs}(s)$ | Spectral Absorption Optical Depth to Path Length s. |
| $\tau_v^{sct}(s)$ | Spectral Scattering Optical Depth to Path Length s. |
| $\tau_v^{vert}(s)$ | Vertical Spectral Extinction Optical Depth to Path Length s. |
| $\tau^{\downarrow}$ | Nadir Optical Depth from TOA. |
| $\tau_p^{\downarrow}$ | Nadir Optical Depth from TOA to Level p. |
| $X_v$ | CO$_2$ line shape sub-Lorentzian multiplicative correction factor. |
| $\Omega_s$ | Solid Angle at Path Length s [sr]. |
| $\omega_{\tau\downarrow}$ | Single Scattering Albedo at Nadir Optical Depth $\tau^{\downarrow}$. |
| $\omega_p$ | Single Scattering Albedo in Layer p. |
| $\omega'_p$ | Delta-M Single Scattering Albedo in Layer p. |

Although specific features of the invention are shown in some drawings and not others, this is for convenience only as some feature may be combined with any or all of the other features in accordance with the invention.

The invention claimed is:

1. A method for identifying a material located on the Earth's surface from an image of the material captured by an airborne or satellite sensor, comprising:
   capturing an image of the material with an airborne or satellite sensor;
   defining one or more atmospheric conditions associated with the image under which radiation transport parameters, including atmospheric transmittance and radiance, will be determined;
   providing atomic and molecular transition data for a given spectral range and the atmospheric conditions;
   selecting a spectral region to be considered;
   dividing the spectral region into a number of spectral bins that determine the spectral resolution, each bin having a width of less than 1.0 cm$^{-1}$;
   calculating atomic and molecular species line center absorption from at least the equivalent width of the atomic and molecular transitions centered within each spectral bin;
   calculating line tail absorption within each spectral bin from atomic and molecular transitions not centered within the bin;
   determining atomic and molecular species spectral transmittances for each spectral bin, the spectral transmittance having a value which is a function of at least the calculated line center absorptions and the calculated line tail absorptions; and
   applying the determined spectral transmittances to the image to identify the material.

2. The method of claim 1 wherein the spectral bins have a width of about 0.1 cm$^{-1}$.

3. The method of claim 1 wherein the calculating line center absorption step includes calculating, from an exact expansion, the bin Voigt equivalent width of atomic and molecular transitions whose centers lie within each spectral bin.

4. The method of claim 3 wherein the exact expansion is an exact modified Bessel functions expansion.

5. The method of claim 3 wherein the calculating line tail absorption step includes subtracting line-tail absorption as calculated from the column strength, the Lorentz half-width, the Doppler half-width, and the line tail spectral displacement.

6. The method of claim 3 wherein the calculating line center absorption step includes determining the Voigt lineshape function computed at specific frequencies.

7. The method of claim 1 wherein the line tail absorption calculation step includes calculating line tail absorption within each bin from atomic and molecular transitions centered outside of the bin using Padé approximant spectral fits to Voigt absorption coefficient curves.

8. The method of claim 7 wherein the line tail absorption calculation step includes determining a database of temperature and pressure dependent Padé approximant spectral fits to Voigt absorption coefficient curves.

9. The method of claim 8 wherein there are five Padé parameters.

10. The method of claim 8 wherein Padé parameters are determined from summed line tail spectral absorption coefficients.

11. The method of claim 10 wherein one Padé parameter is determined at the center of the bin, and one at each edge of the bin.

12. The method of claim 10 wherein one Padé parameter is the derivative of the absorption coefficient with respect to the normalized spectral variable at the line center.

13. The method of claim 10 wherein one Padé parameter is the integral of the spectral absorption coefficient over the spectral band.

14. The method of claim 8 wherein the Padé parameters database is generated for a plurality of temperatures.

15. The method of claim 8 wherein the Padé parameters database is determined for a plurality of pressures.

16. The method of claim 1 wherein the line center absorptions are calculated from atomic and molecular transitions centered no more than half a spectral bin width from the bin, and the line tail absorptions are calculated from atomic and molecular transitions not centered within a half spectral bin from the bin.

17. The method of claim 1 wherein the conditions comprise atmospheric species for which transition data is provided.

18. The method of claim 17 wherein band model data is provided for at least some of the species.

19. The method of claim 18 wherein absorption cross section data is provided for at least some of the species.

20. The method of claim 17 wherein the conditions comprise an arbitrary quantity of species for which transition data is provided.

21. The method of claim 1 wherein the conditions comprise a surface water model.

22. The method of claim 21 wherein the surface water model introduces a spectral attenuation layer.

23. The method of claim 21 wherein the surface water model predicts surface leaving radiances due to surface water.

24. The method of claim 1 wherein the defining step comprises allowing the user to define a radiation refractive path through the atmosphere.

25. The method of claim 24 wherein the refractive path comprises a circular arc.

26. The method of claim 1 wherein the conditions comprise aerosol spectral optical properties.

27. The method of claim 26 wherein the properties can be varied as a function of altitude.

28. The method of claim 26 wherein the properties comprise spectral extinction, spectral scattering and spectral phase function.

29. The method of claim 1 further comprising determining the medium embedded diffuse transmittance.

30. A method for identifying a material located on the Earth's surface from an image of the material captured by an airborne or satellite sensor, comprising:
   receiving an image of the material captured with an airborne or satellite sensor;
   defining one or more atmospheric conditions associated with the image under which radiation transport parameters, including atmospheric transmittance and radiance, will be determined;
   providing atomic and molecular transition data for the spectral range and the atmospheric conditions;
   selecting a spectral region to be considered;
   dividing the spectral region into a number of spectral bins that determine the spectral resolution, each bin having a width of less than $1.0\ cm^{-1}$;
   calculating atomic and molecular species line center absorption from at least the equivalent width of the atomic and molecular transitions centered within each spectral bin;
   calculating line tail absorption within each spectral bin from atomic and molecular transitions not centered within the bin;
   determining atomic and molecular species spectral transmittances for each spectral bin, the spectral transmittance having a value which is a function of at least the calculated line center absorptions and the calculated line tail absorptions; and
   applying the determined spectral transmittances to the image to identify the material.

31. A method for correcting an image of the Earth's surface captured by an airborne or satellite sensor, comprising:
   capturing an image of the Earth's surface with an airborne or satellite sensor;
   defining one or more atmospheric conditions associated with the image under which radiation transport parameters, including atmospheric transmittance and radiance, will be determined;
   providing atomic and molecular transition data for the spectral range and the atmospheric conditions;
   selecting a spectral region to be considered;
   dividing the spectral region into a number of spectral bins that determine the spectral resolution, each bin having a width of less than $1.0\ cm^{-1}$;
   calculating atomic and molecular species line center absorption from at least the equivalent width of the atomic and molecular transitions centered within each spectral bin;
   calculating line tail absorption within each spectral bin from atomic and molecular transitions not centered within the bin;
   determining atomic and molecular species spectral transmittances for each spectral bin, the spectral transmittance having a value which is a function of at least the calculated line center absorptions and the calculated line tail absorptions; and
   applying the determined spectral transmittances to the image to correct the image for the atmospheric conditions.

32. A method for correcting an image of the Earth's surface captured by an airborne or satellite sensor, comprising:
   receiving an image of the Earth's surface captured with an airborne or satellite sensor;
   defining one or more atmospheric conditions associated with the image under which radiation transport parameters, including atmospheric transmittance and radiance, will be determined;
   providing atomic and molecular transition data for the spectral range and the atmospheric conditions;
   selecting a spectral region to be considered;
   dividing the spectral region into a number of spectral bins that determine the spectral resolution, each bin having a width of less than $1.0\ cm^{-1}$;
   calculating atomic and molecular species line center absorption from at least the equivalent width of the atomic and molecular transitions centered within each spectral bin;
   calculating line tail absorption within each spectral bin from atomic and molecular transitions not centered within the bin;
   determining atomic and molecular species spectral transmittances for each spectral bin, the spectral transmittance having a value which is a function of at least the calculated line center absorptions and the calculated line tail absorptions; and
   applying the determined spectral transmittances to the image to correct the image for the atmospheric conditions.

* * * * *